(12) United States Patent
Lengauer et al.

(10) Patent No.: US 9,546,171 B2
(45) Date of Patent: Jan. 17, 2017

(54) PREPARATION OF ERTAPENEM INTERMEDIATES

(71) Applicant: Sandoz AG, Basel (CH)

(72) Inventors: Hannes Lengauer, Kundl (AT); Birgit Endl, Kundl (AT); Wolfgang Felzmann, Kundl (AT)

(73) Assignee: Sandoz AG, Basel (CH)

( * ) Notice: Subject to any disclaimer, the term of this patent is extended or adjusted under 35 U.S.C. 154(b) by 0 days.

(21) Appl. No.: 14/434,550

(22) PCT Filed: Oct. 11, 2013

(86) PCT No.: PCT/EP2013/071252
§ 371 (c)(1),
(2) Date: Apr. 9, 2015

(87) PCT Pub. No.: WO2014/057079
PCT Pub. Date: Apr. 17, 2014

(65) Prior Publication Data
US 2015/0274732 A1    Oct. 1, 2015

(30) Foreign Application Priority Data

Oct. 12, 2012 (EP) .................................... 12188351

(51) Int. Cl.
*C07D 477/08* (2006.01)
*C07D 477/20* (2006.01)
(52) U.S. Cl.
CPC ........... *C07D 477/20* (2013.01); *C07D 477/08* (2013.01); *C07B 2200/13* (2013.01)
(58) Field of Classification Search
CPC .. C07B 2200/13; C07D 477/08; C07D 477/20
See application file for complete search history.

(56) References Cited

U.S. PATENT DOCUMENTS 5,872,250 A    2/1999    Williams et al.

FOREIGN PATENT DOCUMENTS

| CN | 101935321 | * | 1/2011 | ........... C07D 477/06 |
| CN | 101935321 A | | 1/2011 | |
| IN | 1890/CHENP/2007 | | 6/2008 | |
| KR | 2012-0007331 A | | 1/2012 | |
| WO | WO 93/15078 A1 | | 8/1993 | |
| WO | WO 98/02439 A1 | | 1/1998 | |
| WO | WO 98/57973 A1 | | 12/1998 | |
| WO | WO 03/026572 A2 | | 4/2003 | |
| WO | WO 2008/062279 A2 | | 5/2008 | |
| WO | WO 2012/139414 A1 | | 10/2012 | |

OTHER PUBLICATIONS

West, Anthony R., Solid State Chemistry and Its Applications, Wiley, New York, 1988, 358.*
Zhang, et al., Synthesis of carbapenem antibiotic ertapenem, J. of China Pharm. U., 38(4), 305-310 (2007).*
Zhang et al., Synthesis of carbapenem antibiotic ertapenem. Journal of China Pharmaceutical University. Jan. 1, 2007; 38(4):305-310.

* cited by examiner

*Primary Examiner* — Erich A Leeser
(74) *Attorney, Agent, or Firm* — Wolf, Greenfield & Sacks, P.C.

(57) ABSTRACT

The present invention relates to the preparation of compounds, in particular to the preparation of compounds which may be used as intermediates for the preparation of antibiotics, preferably carbapenem antibiotics, more preferably ertapenem, and salts thereof.

8 Claims, 1 Drawing Sheet

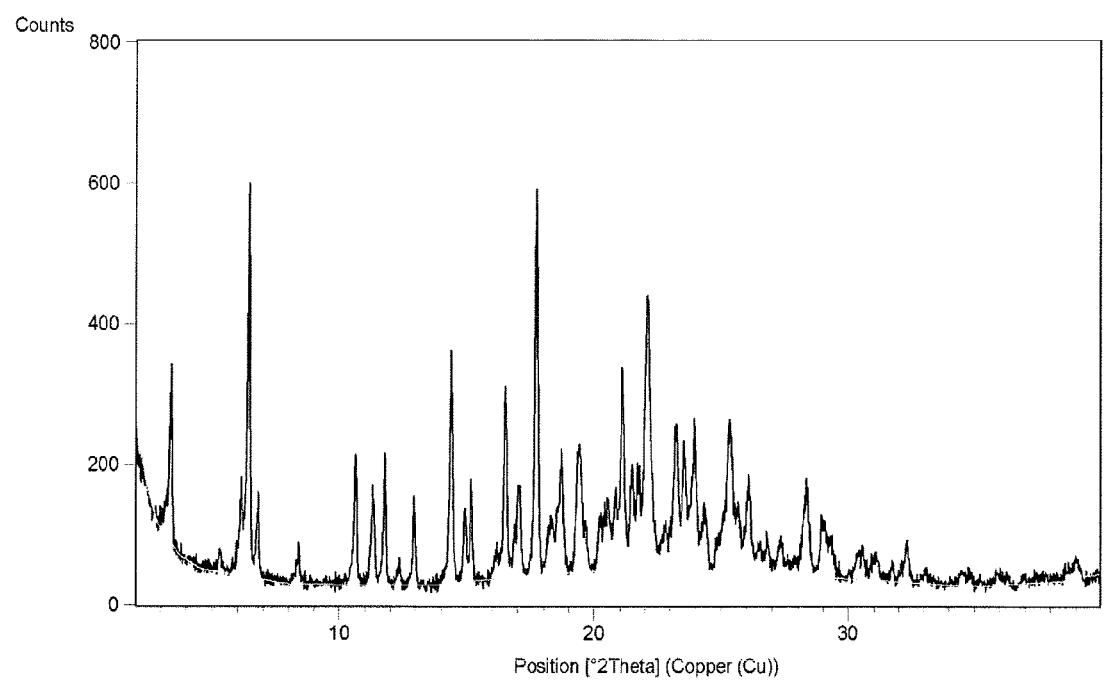

PREPARATION OF ERTAPENEM INTERMEDIATES

RELATED APPLICATIONS

This application is a national stage filing under 35 U.S.C. 371 of International Application PCT/EP2013/071252 entitled "PREPARATION OF ERTAPENEM INTERMEDIATES" filed Oct. 11, 2013, which claims priority to EP Application No. 12188351.6, filed Oct. 12, 2012, the entire disclosure of each of which is incorporated by reference herein in its entirety.

The present invention relates to the preparation of compounds, in particular to the preparation of compounds which may be used as intermediates for the preparation of antibiotics, preferably carbapenem antibiotics, more preferably ertapenem, and salts thereof.

BACKGROUND PRIOR ART

Ertapenem (CAS Registry Number 153832-46-3; IUPAC Name: (4R,5S,6S)-3-[(3S,5S)-5-[(3-carboxyphenyl)carbamoyl]pyrrolidin-3-yl]sulfanyl-6-(1-hydroxyethyl)-4-methyl-7-oxo-1-azabicyclo[3.2.0]hept-2-ene-2-carboxylic acid) is a carbapenem antibiotic by the structure:

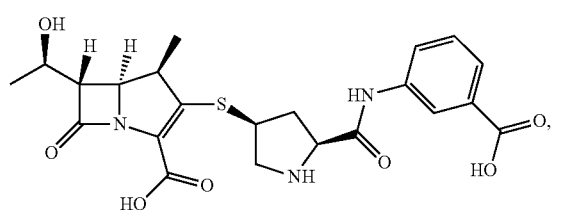

(VI)

Ertapenem is used to treat infectious bacteria, including gram positive and gram negative, aerobic and anaerobic bacteria.

WO 9857973 A1 discloses a process wherein ertapenem is obtained after the preparation of a monoprotected intermediate and subsequent deprotection via hydrogenation. In WO 9802439 A1 the preparation of a multiple protected intermediate of a carbapenem compound in an aprotic, polar solvent in the presence of a base is described. WO 2008062279 A2 discloses a process for the preparation of a diprotected, amorphous intermediate of ertapenem followed by deprotection and isolation of amorphous ertapenem. In WO 03026572 A2 a crystalline form A of the monosodium salt of ertapenem and its preparation by means of crystallization starting from a aqueous ertapenem solution and addition of organic solvents, pH value adjustment and addition of anti-solvents. IN 018900H2007 discloses the preparation of amorphous ertapenem starting from an aqueous ertapenem solution by pH value adjustment, addition of a precipitating agent and anti-solvents.

However, said prior art provides only processes having major drawbacks. For example, the diprotected intermediate obtained in WO 2008062279 A2 is not stable and requires a complicated isolation procedure, which leads to lower yields and the formation of byproducts.

Therefore, there is a constant search for new key intermediates, in particular for new intermediate suitable for the production of ertapenem or its salts, which are obtained, purified and optionally crystallized in a convenient way.

Moreover, there is a constant search for new processes for the preparation of ertapenem or its salts.

Therefore, it was an object of the present invention to provide new key intermediates, in particular new intermediate suitable for the production of ertapenem or its salts, which may be obtained, purified and optionally crystallized in a convenient way.

It was a further object of the present invention to provide new key intermediates in crystalline form, in particular new intermediate suitable for the production of ertapenem or its salts, which may be obtained, purified and crystallized in a convenient way.

It was another object of the present invention to provide a process for the preparation of such key intermediates, in particular such intermediates suitable for the production of ertapenem or its salts.

It was another object of the present invention to provide a process for the preparation of such key intermediates in crystalline form, in particular such intermediates in crystalline form suitable for the production of ertapenem or its salts.

It was a further object of the present invention to provide a process for the preparation of such key intermediates, in particular such intermediates suitable for the production of ertapenem or its salts from known starting materials, e.g. the starting materials used in WO 2008062279 A2.

It was a further object of the present invention to provide a process for the preparation of such key intermediates in crystalline form, in particular such intermediates in crystalline form suitable for the production of ertapenem or its salts from known starting materials, e.g. the starting materials used in WO 2008062279 A2.

It was a further object of the present invention to provide an improved process for the preparation of ertapenem or its salts starting from known starting materials, e.g. the starting materials used in WO 2008062279 A2.

It was another object of the present invention to provide an improved process for the preparation of ertapenem or its salts starting from the new key intermediates.

It was a further object of the present invention to provide an improved process for the preparation of ertapenem or its salts starting from the new key intermediates in crystalline form.

SUMMARY OF THE INVENTION

According to one aspect the present invention relates to a compound of formula (I) or a solvate thereof

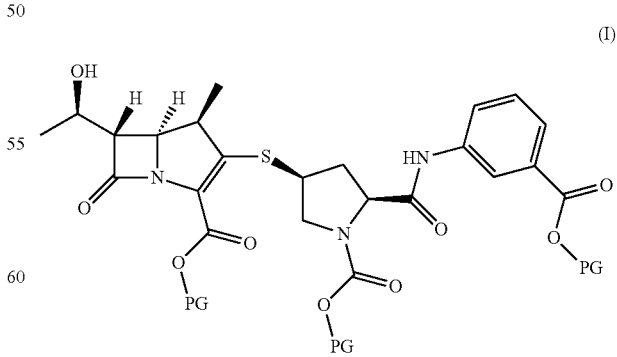

(I)

wherein the PG residues are each and independently a protective group, which is capable of protecting a carboxylic acid function, wherein the PG residues are preferably selected from benzyl protective groups. The compound of formula (I) may be in crystalline or in amorphous form.

According to another aspect of the present invention there is provided a crystalline compound of formula (Ia)

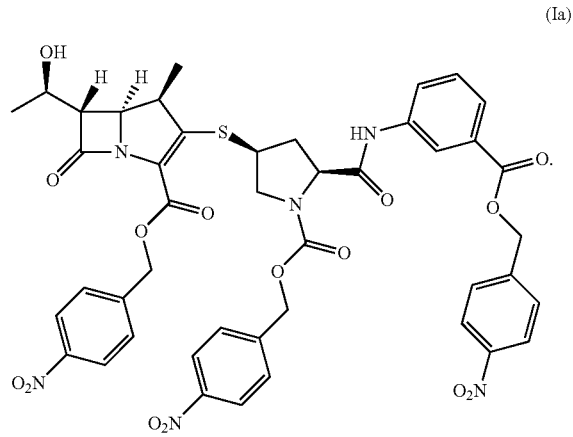 [SMILES: C[C@@H](O)[C@H]1C(=O)N2C(C(=O)OCc3ccc([N+](=O)[O-])cc3)=C(S[C@H]3C[C@@H](C(=O)Nc4cccc(C(=O)OCc5ccc([N+](=O)[O-])cc5)c4)N(C(=O)OCc4ccc([N+](=O)[O-])cc4)C3)[C@H](C)[C@H]12]

(Ia)

According to yet another aspect of the present invention there is provided a crystalline compound of formula (Ia) obtained or obtainable by a process as defined herein.

According to a further aspect of the present invention there is provided the use of a compound of formula (I) or a solvate thereof as defined herein in a process for the preparation of (4R,5S,6S)-3-[(3S,5S)-5-[(3-carboxyphenyl)carbamoyl]-pyrrolidin-3-yl]sulfanyl-6-(1-hydroxyethyl)-4-methyl-7-oxo-1-azabicyclo[3.2.0]hept-2-ene-2-carboxylic acid or a salt thereof.

According to another aspect of the present invention there is provided the use of a compound of formula (I) or a solvate thereof as defined herein in a process for the preparation of (4R,5S,6S)-3-[(3S,5S)-5-[(3-carboxyphenyl)carbamoyl]-pyrrolidin-3-yl]sulfanyl-6-(1-hydroxyethyl)-4-methyl-7-oxo-1-azabicyclo[3.2.0]hept-2-ene-2-carboxylic acid or a salt thereof starting from the following compounds of formula (II) and (III) or a salt thereof

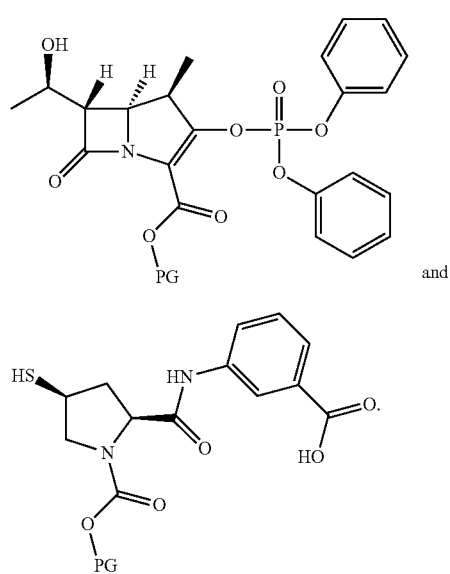

(II)

and (III)

In still another aspect, there is provided a process for the preparation of a compound of formula (I) or a solvate as defined herein thereof comprising a step a) of reacting a compound of formula (II),

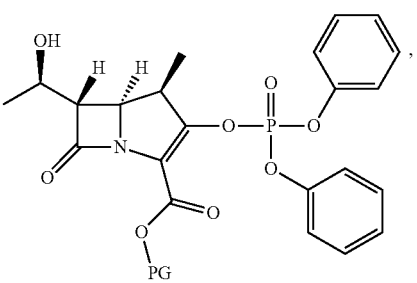

(II)

with a compound of formula (III) or a salt thereof,

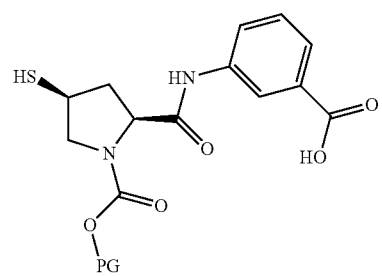

(III)

to obtain a compound of formula (IV) or a salt thereof

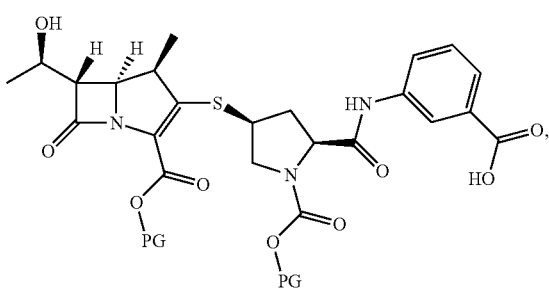

(IV)

and a step b) of converting the compound of formula (IV) or a salt thereof to the compound of formula (I) or a solvate thereof, and optionally a step c) of crystallizing the compound of formula (I) or a solvate thereof from a solution of the compound of formula (I).

According to a further aspect of the present invention there is provided a process for the preparation of a compound of formula (VI) or a salt thereof, preferably its monosodium salt of formula (VII), (VI)

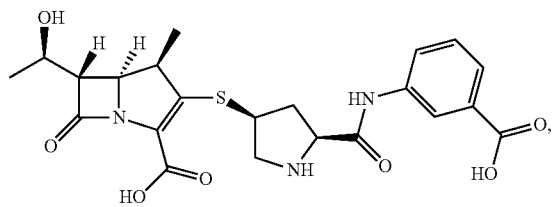

(VII)

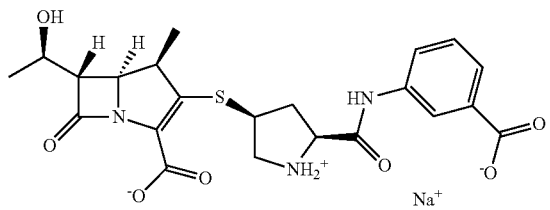

comprising a step a) of reacting a compound of formula (II), (II)

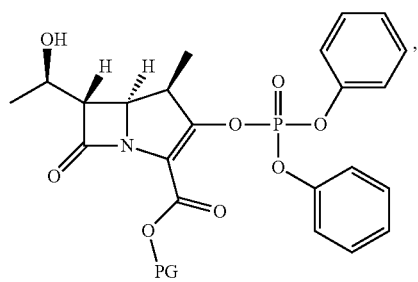

with a compound of formula (III) or a salt thereof, (III)

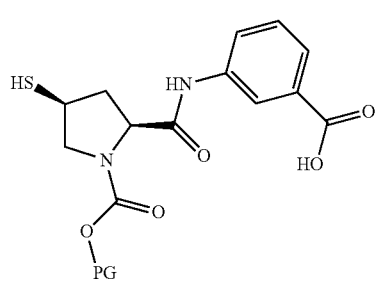

to obtain a compound of formula (IV) or a salt thereof (IV)

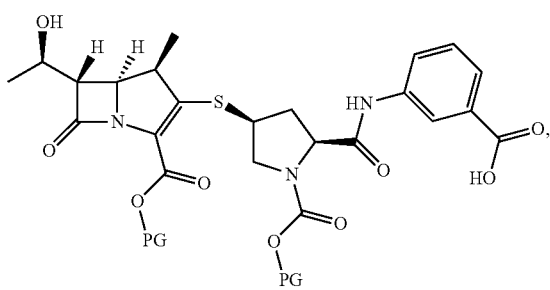

and a step b) of converting the compound of formula (IV) or a salt thereof to a compound of formula (I) or a solvate thereof as defined herein;
and a step d) of converting the compound of formula (I) or a solvate thereof to the compound of formula (VI) or a salt thereof, preferably its monosodium salt (VII), optionally after a step c) of crystallizing the compound of formula (I) or a solvate thereof from a solution of the compound of formula (I).

In yet another aspect of the present invention there is provided a process for the preparation of a compound of formula (I) or a solvate thereof as defined herein; comprising a step b) of converting a compound of formula (IV) or a salt thereof (IV)

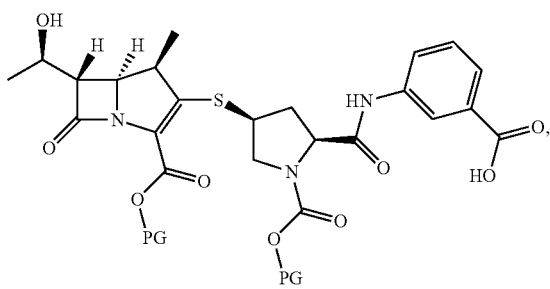

to the compound of formula (I) or a solvate thereof, and optionally a step c) of crystallizing the compound of formula (I) or a solvate thereof from a solution of the compound of formula (I).

According to a further aspect of the present invention there is provided a process for the preparation of a compound of formula (VI) or a salt thereof, preferably its monosodium salt of formula (VII), (VI)

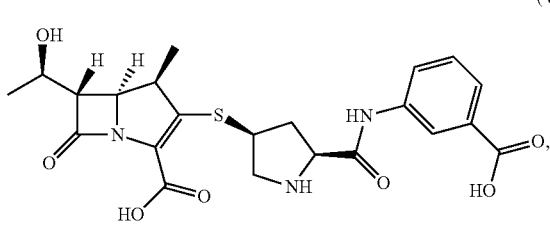

-continued

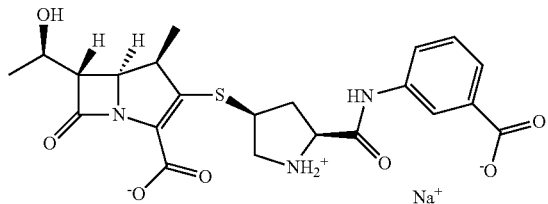

(VII)

comprising a step b) of converting a compound of formula (IV) or a salt thereof

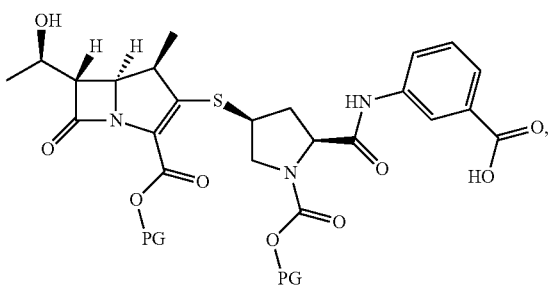

(IV)

to a compound of formula (I) or a solvate thereof as defined herein;
and a step d) of converting the compound of formula (I) or a solvate thereof
to the compound of formula (VI) or a salt thereof, preferably its monosodium salt, optionally after a step c) of crystallizing the compound of formula (I) or a solvate thereof from a solution of the compound of formula (I).

In still another aspect, there is provided a process for the preparation of a compound of formula (VI) or a salt thereof, preferably its monosodium salt of formula (VII)

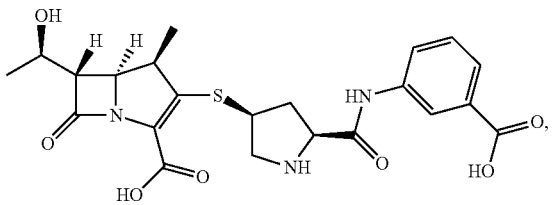

(VI)

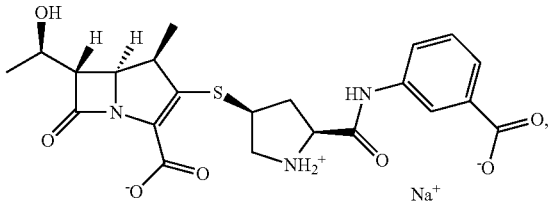

(VII)

comprising a step d) of converting a compound of formula (I) or a solvate thereof as defined herein; to the compound of formula (VI) or a salt thereof; optionally after a step c) of crystallizing the compound of formula (I) or a solvate thereof from a solution of the compound of formula (I).

In yet another aspect of the present invention there is provided a process for the preparation of a compound of formula (I) as defined herein, in crystalline form, comprising a step c) of crystallizing the compound of formula (I) from a solution of the compound of formula (I).

The present invention represents an improvement over the known key intermediates for the production of ertapenem or its salts, as the compounds of formula (I) as defined herein may be obtained and purified in a convenient way. In particular, the compounds of formula (I) are isolable, which results in lower amounts of side products being present during the later production of ertapenem or its salts. Some of the compounds of formula (I), e.g. the compound of formula (Ia), may have the advantage that they can be crystallized.

DEFINITIONS

The term "protective group" as used herein shall be understood as known in the art. In particular, it shall be understood as a group which has been introduced into a molecule by chemical modification of a functional group of the molecule to avoid a reaction of said functional group in a subsequent reaction. The "protective group" is introduced in to the molecule by a reaction of a functional group of the molecule and an "agent suitable for introducing a in protective group". An "agent suitable for removing the protective group or the PG residue" as used herein shall be understood as known in the art. In particular, it shall be understood as an agent, which cleaves the "protective group" from the said functional group and allows the functional group to react in a subsequent reaction. A "protective group" that is "capable of protecting a carboxylic acid function" as used herein shall be understood as a protective group which avoids a reaction of said carboxylic acid function under the conditions of a step a) and/or a step b) as defined herein, especially as exemplified in the examples. In particular, a "protective group" that is "capable of protecting a carboxylic acid function" avoids between 95 to 100%, particularly between 98 to 100%, more particularly 100%, of a reaction of said carboxylic acid function under basic conditions, in an aprotic solvent, particularly DMAc (2M), at a temperature between −20° C. to 35° C., for 2 to 5 hours, in the absence of an "agent suitable for removing the protective group or the PG residue", e.g. hydrogen when the "protective group" is a benzylic group. A "protective group" that is "capable of protecting a carboxylic acid function" may thus also be understood as a protective group" that "protects a carboxylic acid function", especially under the conditions of a step a) and/or a step b) as defined herein, especially as exemplified in the examples, particularly as a group that "protects a carboxylic acid function" by avoiding between 95 to 100%, particularly between 98 to 100%, more particularly 100%, of a reaction of said carboxylic acid function under basic conditions, in an aprotic solvent, particularly DMAc (2M), at a temperature between −20° C. to 35° C., for 2 to 5 hours, in the absence of an "agent suitable for removing the protective group or the PG residue", e.g. hydrogen when the "protective group" is a benzylic group.

The term "seeding crystal" as used herein shall be understood as known in the art. In particular, it shall be understood as a small amount of crystalline material from which a large amount of same crystalline material is grown.

The term "halide" or "halogen" as used herein shall be understood as including at least chlorine, iodine, and bromine.

The term "leaving group" as used herein shall be understood as known in the art. Suitable leaving groups are listed for example in standard text books such as March's Advanced Organic Chemistry: Reactions, Mechanisms, and Structure, 6th Edition; Wiley & Sons. Preferred leaving groups are halides, particularly bromide, alkyl sulfonates and aryl sulfonates, and is preferably bromide.

The term "without purification and/or isolation" as used herein shall be understood as describing a process or step in which a compound is obtained in a first step and converted in a second step, wherein the compound is not purified and/or isolated between the first and the second step.

The terms "ambient temperature" and "room temperature" used herein will be understood by the person skilled in the art as referring to a temperature between about 20° C. and about 25° C., particularly between 20° C. and 25° C.

BRIEF DESCRIPTION OF DRAWINGS

FIG. 1 is a diagram showing X-ray powder diffraction pattern of crystalline compound of formula (Ia) with Copper (Cu)—Kα radiation.

DETAILED DESCRIPTION OF THE INVENTION

Compounds of Formula (I)
According to one aspect the present invention relates to a compound of formula (I) or a solvate thereof

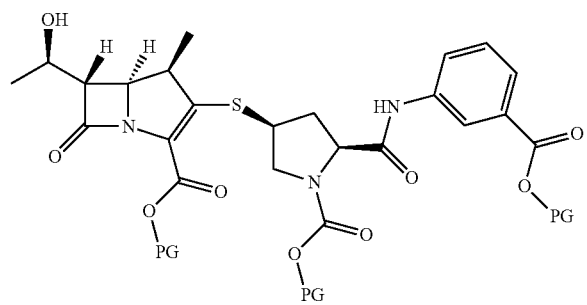

wherein the PG residues are each and independently a protective group, which is capable of protecting a carboxylic acid function, wherein the PG residues are preferably selected from benzyl protective groups. The PG residues may be identical or may be different. It is also possible that only two of the PG residues are identical, e.g. the PG residue attached to the carbapeneme moiety and PG residues attached to the benzoic acid moiety, or the PG residue attached to the carbapeneme moiety and PG residues attached to the pyrrolidine moiety, or the PG residue attached to the benzoic acid moiety and PG residues attached to the pyrrolidine moiety. Preferably, the PG residues are identical.

Each PG residue may be selected from benzyl, methylene substituted benzyl, p-substituted benzyl, o-substituted benzyl, or m-substituted benzyl groups, wherein the substituent is preferably selected from nitro, methoxy residues or halides; wherein the PG residue is more preferably selected from p-nitrobenzyl, o-nitrobenzyl, m-nitrobenzyl, p-methoxybenzyl, o-methoxybenzyl, or m-methoxybenzyl; p-chlorobenzyl, o-chlorobenzyl and is most preferably p-nitrobenzyl.

The compound of formula (I) may be in crystalline or in amorphous form. The compound of formula (I) as defined herein may also be present in form of its solvate. In a particularly preferred embodiment, the compound of formula (I) is the compound of formula (Ia)

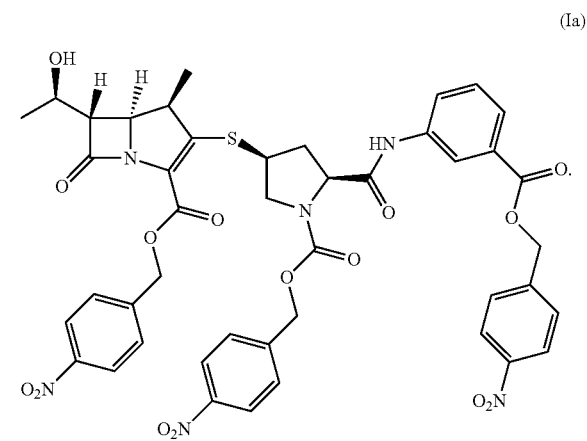 [SMILES: C[C@@H](O)[C@H]1C(=O)N2C(C(=O)OCc3ccc([N+](=O)[O-])cc3)=C(S[C@H]3C[C@@H](C(=O)Nc4cccc(C(=O)OCc5ccc([N+](=O)[O-])cc5)c4)N(C(=O)OCc4ccc([N+](=O)[O-])cc4)C3)[C@H](C)[C@H]12]

In another particularly preferred embodiment, the compound of formula (I) is the crystalline compound of formula (Ia). In a particularly preferred embodiment, the crystalline compound of formula (Ia) is characterized by an X-ray powder diffraction pattern with peaks at 2-theta angels of about 3.4°, 6.5°, 14.4°, 17.7°, 21.1°, 22.1° when using Cu—Kα radiation (see also FIG. 1). The crystalline compound of formula (Ia) is typically obtained or obtainable by a process as defined herein.

The compounds of formula (I) or a solvate thereof may be used in a process for the preparation of (4R,5S,6S)-3-[(3S,5S)-5-[(3-carboxyphenyl)carbamoyl]-pyrrolidin-3-yl]sulfanyl-6-(1-hydroxyethyl)-4-methyl-7-oxo-1-azabicyclo[3.2.0]hept-2-ene-2-carboxylic acid (formula (VI)) or a salt thereof, preferably the monosodium salt of formula (VII).

The compounds of formula (I) or a solvate thereof may also be used in a process for the preparation of (4R,5S,6S)-3-[(3S,5S)-5-[(3-carboxyphenyl)carbamoyl]-pyrrolidin-3-yl]sulfanyl-6-(1-hydroxyethyl)-4-methyl-7-oxo-1-azabicyclo[3.2.0]hept-2-ene-2-carboxylic acid (formula (VI)) or a salt thereof, preferably the monosodium salt of formula (VII), starting from the following compounds of formula (II) and (III) or a salt thereof

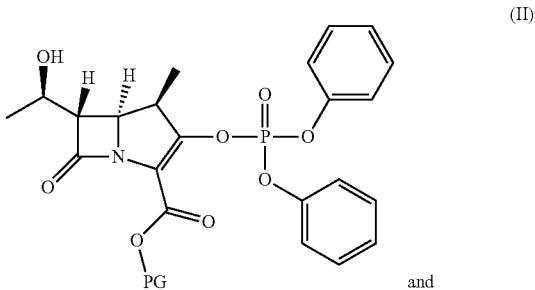

and

-continued (III)

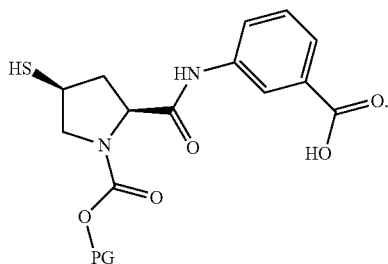

Process for the Preparation of a Compound of Formula (VI)

According to a further aspect, there is provided a process for the preparation of a compound of formula (I) or a solvate thereof (I)

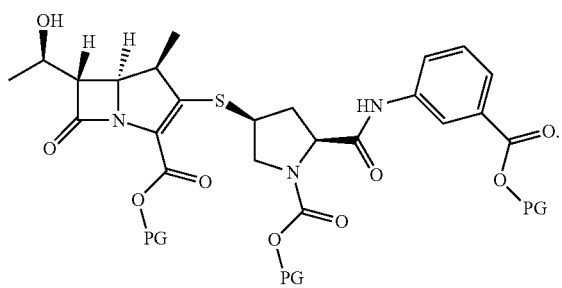

wherein the PG residues are as defined herein; comprising a step a) of reacting a compound of formula (II), (II)

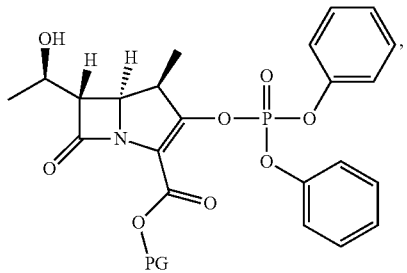

with a compound of formula (III) or a salt thereof, (III)

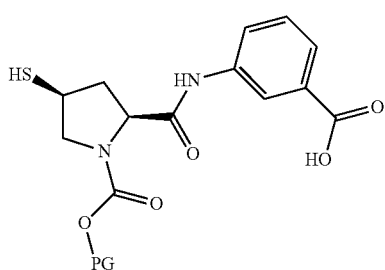

to obtain a compound of formula (IV) or a salt thereof (IV)

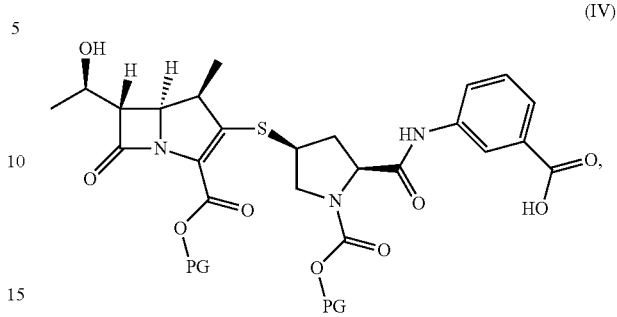

and a step b) of converting the compound of formula (IV) or a salt thereof to the compound of formula (I) or a solvate thereof, and optionally a step c) of crystallizing the compound of formula (I) or a solvate thereof from a solution of the compound of formula (I).

Process for the Preparation of a Compound of Formula (VI)

According to another aspect, there is provided a process for the preparation of a compound of formula (VI) or a salt thereof, preferably its monosodium salt of formula (VII), (VI)

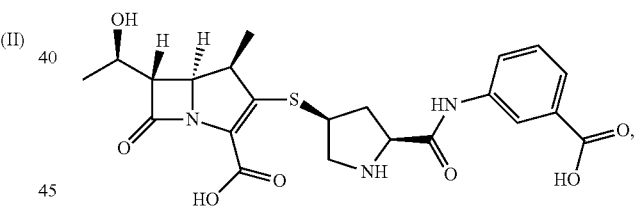

comprising a step a) of reacting a compound of formula (II), (II)

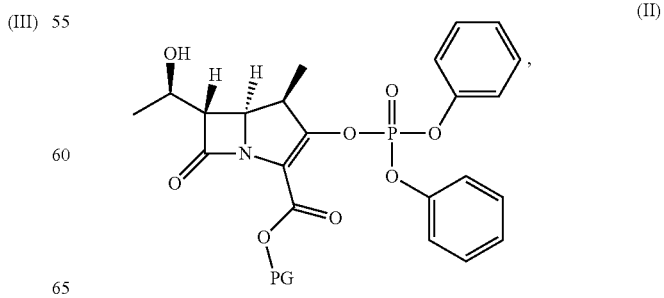

with a compound of formula (III) or a salt thereof, (III)

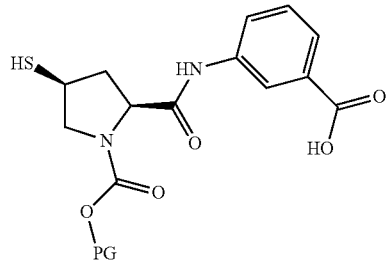

to obtain a compound of formula (IV) or a salt thereof (IV)

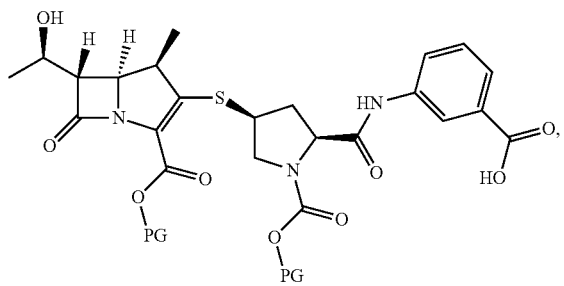

and a step b) of converting the compound of formula (IV) or a salt thereof to a compound of formula (I) or a solvate thereof (I)

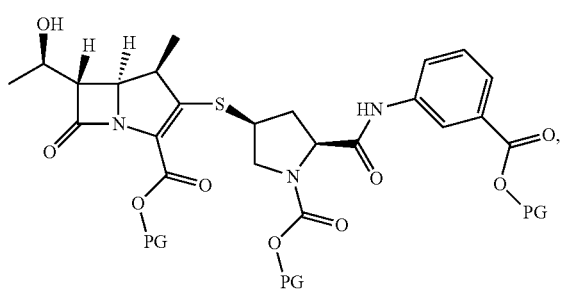

wherein the PG residues are as defined herein; and a step d) of converting the compound of formula (I) or a solvate thereof; to the compound of formula (VI) or a salt thereof, preferably its monosodium salt of formula (VII), optionally after a step c) of crystallizing the compound of formula (I) or a solvate thereof from a solution of the compound of formula (I).

Process for the Preparation of a Compound of Formula (I)

According to another aspect, there is provided a process for the preparation of a compound of formula (I) or a solvate thereof (I)

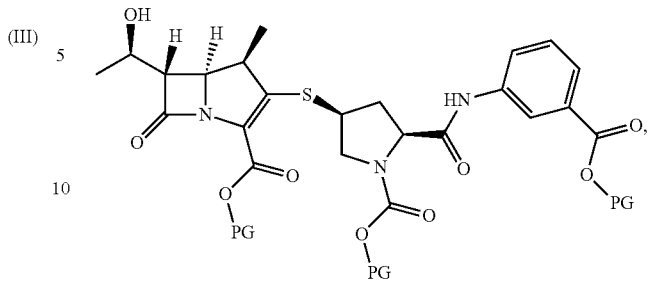

wherein the PG residues are as defined herein; comprising a step b) of converting a compound of formula (IV) or a salt thereof (IV)

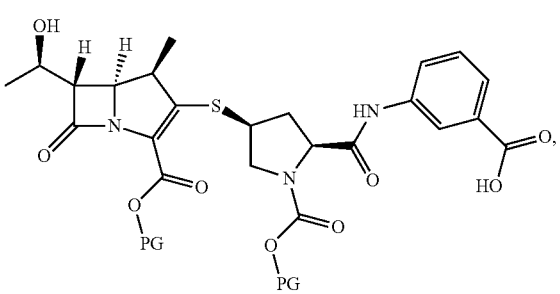

to the compound of formula (I) or a solvate thereof, and optionally a step c) of crystallizing the compound of formula (I) or a solvate thereof from a solution of the compound of formula (I).

Process for the Preparation of a Compound of Formula (VI) Starting from a Compound of Formula (IV)

According to yet another aspect, these is provided a process for the preparation of a compound of formula (VI) or a salt thereof, preferably its monosodium salt of formula (VII), (VI)

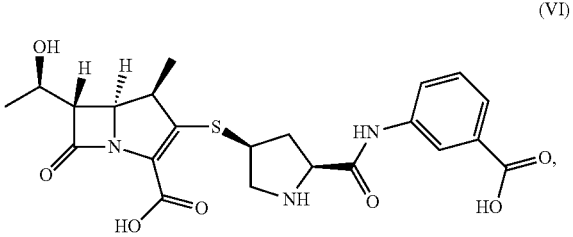 [SMILES: C[C@@H](O)[C@H]1C(=O)N2C(C(=O)O)=C(S[C@@H]3CN[C@H](C(=O)Nc4cccc(C(=O)O)c4)C3)[C@H](C)[C@H]12]

comprising a step b) of converting a compound of formula (IV) or a salt thereof

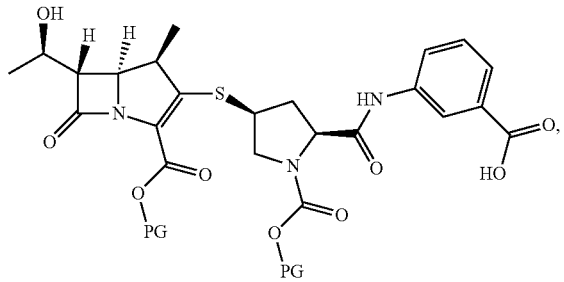

to a compound of formula (I) or a solvate thereof

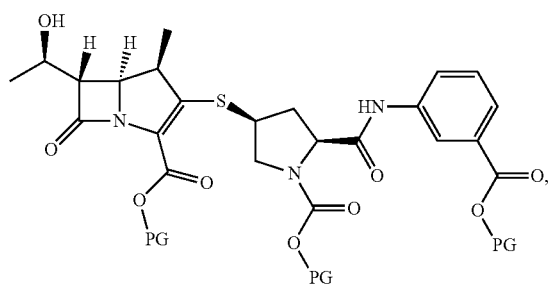

wherein the PG residues are as defined herein; and a step d) of converting the compound of formula (I) or a solvate thereof; to the compound of formula (VI) or a salt thereof, preferably its monosodium salt (VII), optionally after a step c) of crystallizing the compound of formula (I) or a solvate thereof from a solution of the compound of formula (I).

Process for the Preparation of a Compound of Formula (VI) Starting from a Compound of Formula (I)

According to a further aspect, these is provided a process for the preparation of a compound of formula (VI) or a salt thereof, preferably its monosodium salt (VII),

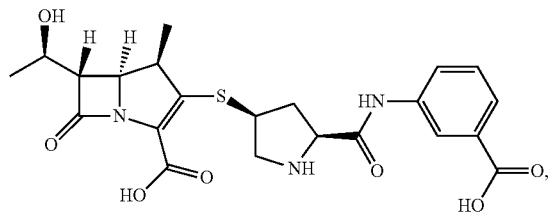

comprising a step d) of converting a compound of formula (I) or a solvate thereof

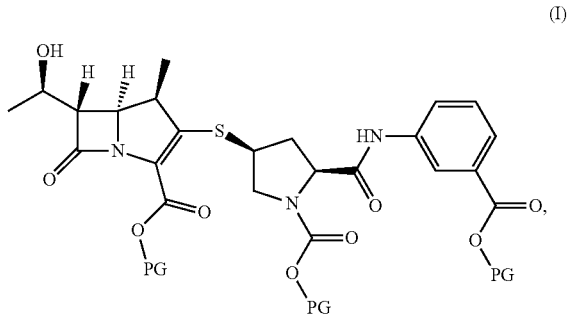

wherein the PG residues are as defined herein; to the compound of formula (VI) or a salt thereof; optionally after a step c) of crystallizing the compound of formula (I) or a solvate thereof from a solution of the compound of formula (I). According to a preferred embodiment, the compound of formula (I) is the compound of formula (Ia) as defined herein. Optionally, the compound of formula (IV) is used after step a) without purification and/or isolation of the compound of formula (IV) after step a). In addition, the compound of formula (I) is optionally used after step b) without purification and/or isolation of the compound of formula (I) after step b).

Step a)

Typically, step a) is carried out at a temperature of −40° C. to 0° C., particularly from −30° C. to −10° C., and more particularly −20° C. to −15° C. When step a) is carried out in a solvent, the solvent is particularly an aprotic solvent, selected from dimethylacetamide (DMAc), tetrahydrofuran (THF), dimethylformamide (DMF), 2-methyltetrahydrofuran, N-methyl-2-pyrrolidone (NMP), and any combination thereof, and is particularly DMAc. The compound of formula (III) or a salt thereof is typically present in an amount of 1.0 to 1.3 equivalents, particularly of 1.0 to 1.2 equivalents, and more particularly 1.09 equivalents, with respect to the compound of formula (II). Step a) is typically carried out in the presence of a base, which is typically selected from secondary and tertiary amines, particularly isopropylmethylamine, butylmethylamine, diisopropylethylamine and triethylamine; cyclic tertiary amines, particularly cis-2,6-dimethylpiperidine, 1,4-diazabicyclo[2.2.2]octane, N-methylpiperidine and N-methylmorpholine; and any combination thereof, and is preferably diisopropylethylamine. The base is then present in an amount of 2 to 6 equivalents, particularly of 4 to 5 equivalents, and more particularly 4.4 equivalents, with respect to the compound of formula (II).

According to a preferred embodiment, when the compound of formula (I) is the compound of formula (Ia)

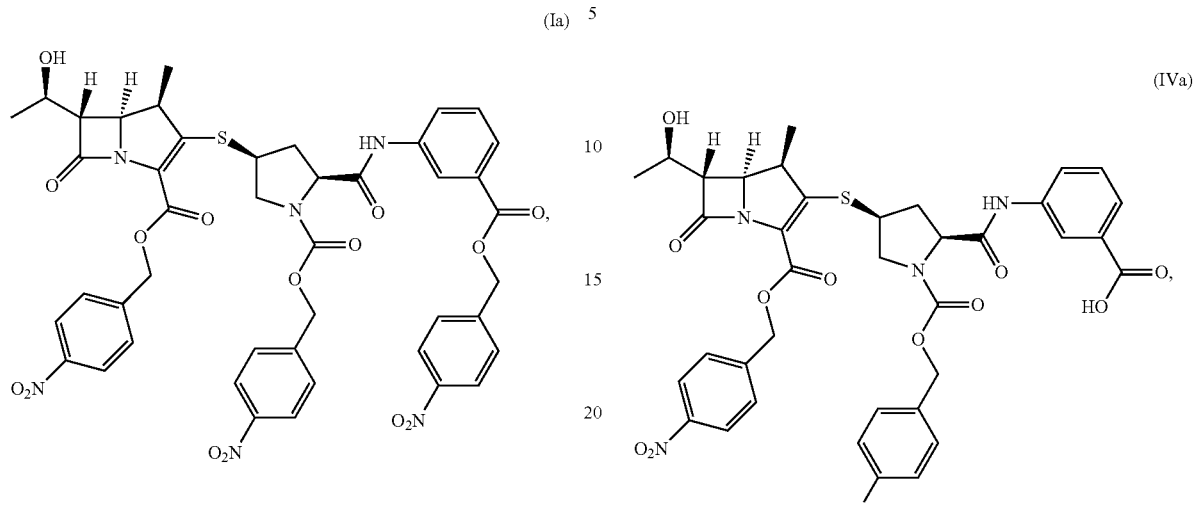

step a) comprises reacting a compound of formula (IIa),

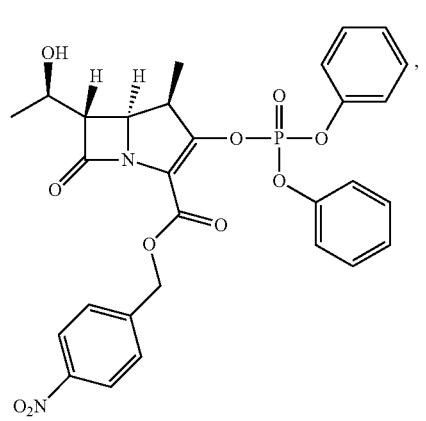

with a compound of formula (IIIa),

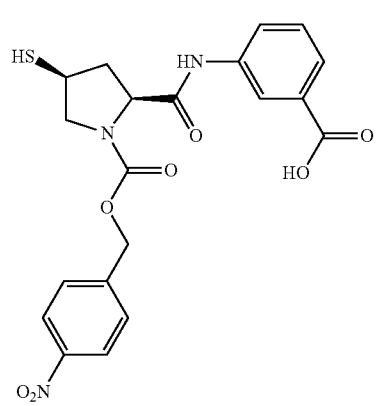

to obtain a compound of formula (IVa)

and step a) is carried out with 1.09 equivalents of the compound of formula (IIIa) in the presence 4.4 equivalents of diisopropylethylamine, each with respect to the compound of formula (IIa); at a temperature of −20° C. in DMAc.

Step b)

According to one embodiment the compound of formula (IV) or a salt thereof is converted in step b) to the compound of formula (I) without purification and/or isolation of the compound of formula (IV) or a salt thereof after step a). Step b) is then typically carried out at a temperature of 10° C. to 45° C., particularly from 30° C. to 40° C., and more particularly at 35° C. Converting the compound of formula (IV) or a salt thereof to the compound of formula (I) or a solvate thereof is then typically carried out by adding an agent suitable for introducing a protective group. The agent suitable for introducing a protective group may be a compound of formula (V)

PG-L       (V)

wherein the PG residues are as defined herein and wherein L is a leaving group, wherein the compound is preferably added in the same solvent as used for step a). L is typically selected from halides, particularly bromide, alkyl sulfonates and aryl sulfonates, and is preferably bromide. When the PG residue is p-nitrobenzyl the compound of formula (V) is selected from p-nitrobenzylbromide and p-nitrobenzylchloride, and is preferably p-nitrobenzylbromide. The compound of formula (V) is then typically present in an amount of 1 to 3 equivalents, particularly of 1.2 to 1.4 equivalents, and more particularly 1.3 equivalents, with respect to the compound of formula (II).

According to one particularly preferred embodiment, when the compound of formula (I) is the compound of formula (Ia)

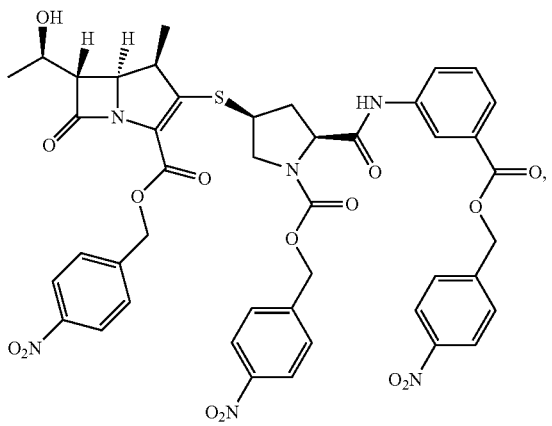

(Ia)

step b) comprises converting a compound of formula (IVa)

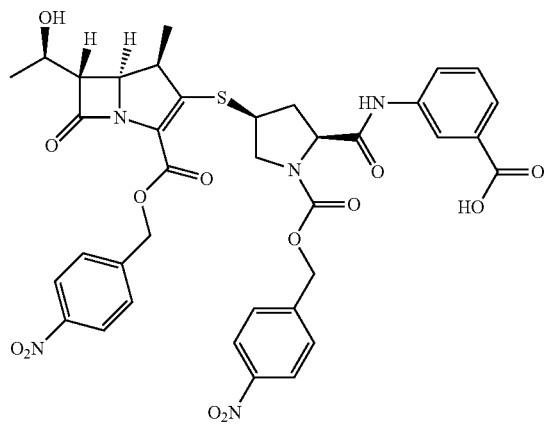

(IVa)

to the compound of formula (Ia), wherein step b) with 1.3 equivalents of p-nitrobenzylbromide with respect to the compound of formula (II); at a temperature of 35° C.

According to another embodiment, the compound of formula (IV) or a salt thereof is converted in step b) to the compound of formula (I) after purification and/or isolation of the compound of formula (IV) or a salt thereof after step a). In step b) the compound of formula (IV) or a salt thereof is present in an amount of 1 equivalent. Step b) is then typically carried out at a temperature of 10° C. to 40° C., particularly from 20° C. to 30° C., and more particularly room temperature. Converting the compound of formula (IV) or a salt thereof to the compound of formula (I) or a solvate thereof is then typically carried out by adding an agent suitable for introducing a protective group. The agent suitable for introducing a protective group may be a compound of formula (V)

PG-L  (V)

wherein the PG residues are as defined herein and wherein L is a leaving group, wherein the compound is preferably added in the same solvent as used for step a). L is typically selected from halides, particularly bromide, alkyl sulfonates and aryl sulfonates, and is preferably bromide. When the PG residue is p-nitrobenzyl the compound of formula (V) is selected from p-nitrobenzylbromide and p-nitrobenzylchloride, and is preferably p-nitrobenzylbromide. The compound of formula (V) is then typically present in an amount of 1.0 to 3.0 equivalents, particularly of 1.2 to 1.4 equivalents, and more particularly 1.3 equivalents, with respect to the compound of formula (IV) or a salt thereof. Step b) is then typically carried out in the presence of a base, wherein the base is then present in an amount of 1.0 to 4.0 equivalents, particularly of 1.5 to 3 equivalents, and more particularly 2 equivalents, with respect to the compound of formula (I) or a solvate thereof. The base is then typically selected from secondary and tertiary amines, particularly isopropylmethylamine, butylmethylamine, diisopropylethylamine and triethylamine; cyclic tertiary amines, particularly cis-2,6-dimethylpiperidine, 1,4-diazabicyclo[2.2.2]octane, N-methylpiperidine and N-methylmorpholine; and any combination thereof, and is preferably triethylamine. When step b) is carried out in a solvent, particularly an aprotic solvent, then the solvent is particularly selected from dimethylformamide (DMF), dimethylacetamide (DMAc), tetrahydrofuran (THF), 2-methyltetrahydrofuran, N-methyl-2-pyrrolidone (NMP), and any combination thereof, and is more particularly DMAc.

According to one particularly preferred embodiment, when the compound of formula (I) is the compound of formula (Ia)

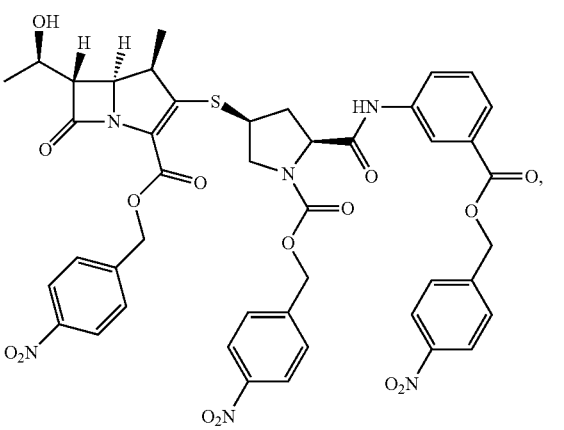

(Ia)

the step b) comprises converting a compound of formula (IVa)

(IVa)

to the compound of formula (Ia), wherein step b) is carried is out with 1.3 equivalents p-nitrobenzylbromide and 1.0 equivalent of a compound of formula (IVa) in the presence of 2 equivalents of triethylamine or diisopropylethylamine, each with respect to the compound of formula (IVa); at room temperature in DMAc.

Process for the Preparation of a Compound of Formula (I) in Crystalline Form

According to a further aspect, it is provided a process for the preparation of a compound of formula (I) as defined herein, particularly a compound of formula (Ia), in crystalline form, comprising a step c) of crystallizing the compound of formula (I) from a solution of the compound of formula (I).

According to one embodiment, step c) comprises a step h) of adding seeding crystals to a solution of a compound of formula (I). The solution typically comprises the compound of formula (I) in a concentration of 0.05 to 0.20 mol/L, particularly of 0.10 to 0.14 mol/L, and more particularly 0.11 mol/L. The solvent used for the solution is typically an aprotic solvent, particularly selected from ethyl acetate and heptane, and any combination thereof, and is more particularly ethyl acetate. Typically, step c) is then carried out at a temperature of −10° C. to 35° C., particularly from 10° C. to 25° C., and more particularly 25° C. According to one particularly preferred embodiment, when the compound of formula (I) is the compound of formula (Ia)

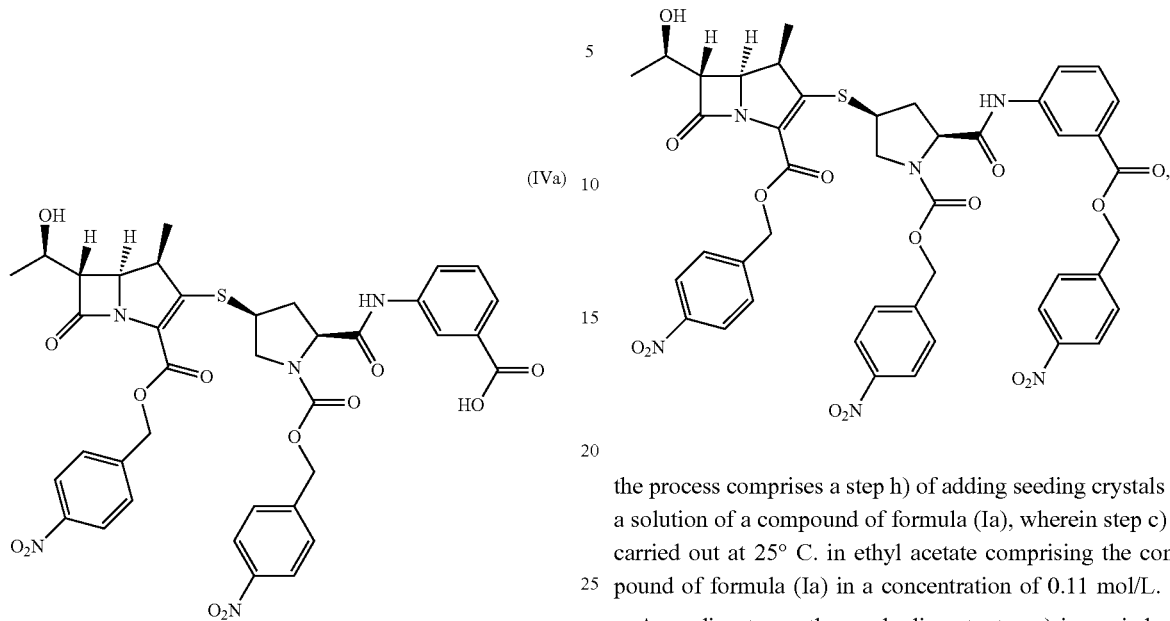

(Ia)

the process comprises a step h) of adding seeding crystals to a solution of a compound of formula (Ia), wherein step c) is carried out at 25° C. in ethyl acetate comprising the compound of formula (Ia) in a concentration of 0.11 mol/L.

According to another embodiment, step c) is carried out without purification and/or isolation of the compound of formula (I) after a step b) as defined above. According to a further embodiment step c) is carried out without purification and/or isolation of the compound of formula (I) or a solvate thereof after step b) has been carried out as defined above and wherein step b) is carried out without purification and/or isolation after a step a) as defined above. In these embodiments the solvent used for the solution is particularly the solvent as used in step b). Further, step c) may comprise a step e), wherein in step e) the concentration of the compound of formula (I) or a solvate thereof in the solution is adjusted to be in the range of 0.14 to 0.3M, particularly of 0.15 to 0.2 M, and more particularly 0.16 M, preferably by adding further solvent used for the solution, preferably DMAc. Even further, step c) may comprises a step f), preferably after a step e) as defined above, wherein in step f) acid is added to quench excess base, wherein the acid is preferably AcOH or HCl, more preferably AcOH. Further, step c) comprises a step g), preferably after a step f) as defined above, wherein in step g) an anti-solvent is added wherein the anti-solvent is preferably selected from isopropyl alcohol, ethyl acetate, n-propanol, ethanol, methanol and water, and any combination thereof, and is preferably isopropyl alcohol and water. Further, step c) may comprise a step h), preferably after a step g) as defined above, of adding seeding crystals to a solution of a compound of formula (I). Step c) is typically carried out at a temperature of 20° C. to 40° C., particularly from 32° C. to 38° C., and more particularly 35° C.

According to one particularly preferred embodiment, when the compound of formula (I) is the compound of formula (Ia)

to obtain a compound of formula (IVa)

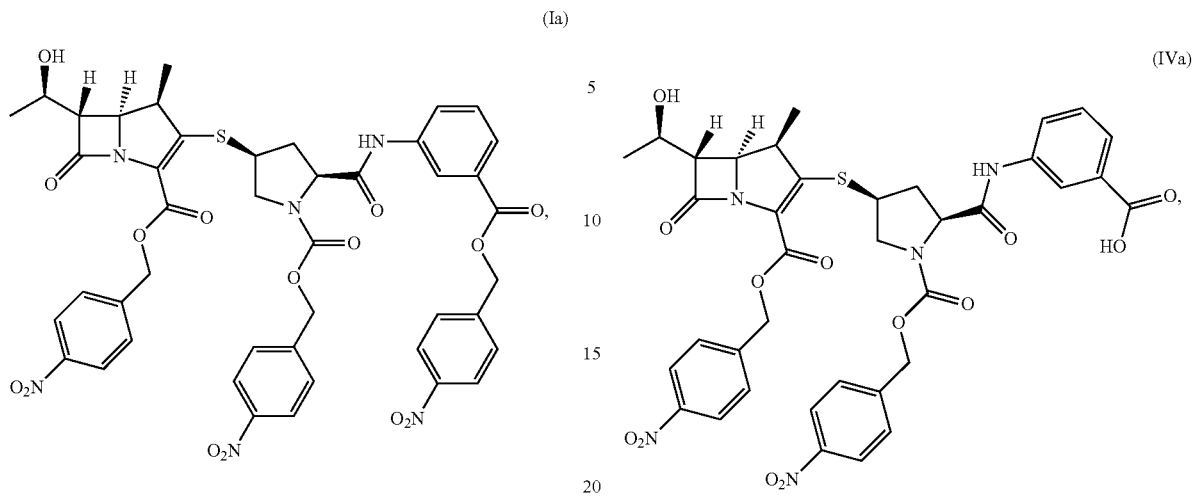
(Ia)
(IVa)

the process comprises a step a) of reacting a compound of formula (IIa),

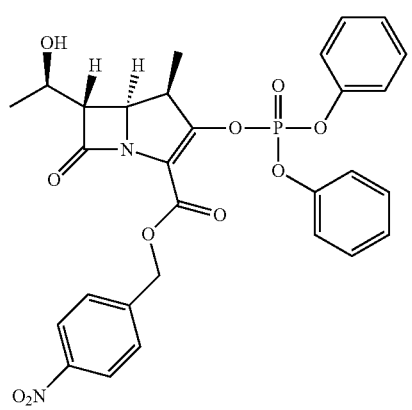
(IIa)

with a compound of formula (IIIa),

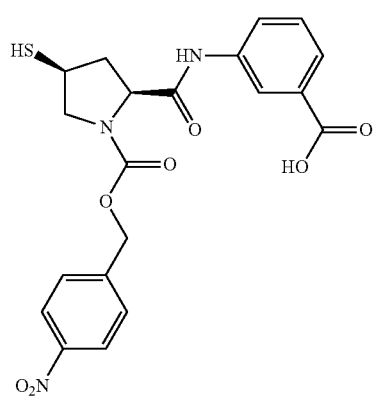
(IIIa)

wherein step a) is carried out with 1 equivalent of the compound of formula (IIa) and 1.09 equivalents of the compound of formula (IIIa) in the presence 4.4 equivalents of diisopropylethylamine, each with respect to the compound of formula (IIa), at a temperature of −20° C. in DMAc;

a step b) of converting the compound of formula (IVa) to the compound of formula (Ia), wherein step b) is carried out with 1.3 equivalents of p-nitrobenzylbromide with respect to the compound of formula (IIa); at 35° C., and wherein the compound of formula (IVa) has been obtained after the step a) and is used without purification and/or isolation of the compound of formula (IVa) after step a); and a step c) of crystallizing the compound of formula (Ia), wherein step c) comprises a step e), wherein in step e) the concentration of the compound of formula (Ia) in the solution is adjusted to be 0.16 M by adding further DMAc;

a step f), wherein in step f) AcOH is added;

a step g), wherein in step g) isopropyl alcohol and water are added; and a step h), wherein in step h) seeding crystals are added at a temperature of 35° C.

Step d

According to all aspects and embodiments provided herein, the compound of formula (VI) may be produced in form of a salt, preferably in form of its sodium, potassium, or lithium salt, more preferably in form of its monosodium salt (formula (VII)).

In step d) typically an agent suitable for removing the PG residues is added. Typically, step d) is carried out in the presence of a catalyst. The agent is particularly hydrogen. The catalyst is then particularly selected from the group of solid-supported metal catalysts, preferably from palladium-on-carbon, platinum-on-carbon, platinum-vanadium-on-carbon, and palladium hydroxid, and is more preferably palladium-on-carbon. Typically, step d) is then carried out in the presence of a base, wherein the base is particularly selected from basic inorganic salts, particularly from sodium hydrogen carbonate, sodium carbonate, potassium carbonate, or calcium acetate, particularly sodium hydrogen carbonate and sodium carbonate; and any combination thereof, and is preferably sodium hydrogen carbonate.

According to one embodiment of step d), the compound of formula (I) is used in crystalline form, particularly as defined herein. Step d) is then carried out in the presence of a base and the base is present in an amount of 3.5 to 7 equivalents, particularly 4.5 to 6.5 equivalents, and more particularly 5.5 equivalents, with respect to the compound of formula (I). Typically, step d) is then carried out at a temperature of 15° C. to 40° C., particularly from 20° C. to 30° C., and more particularly room temperature. When step d) is carried out in a solvent, the solvent is particularly selected from water, tetrahydrofuran, isopropyl alcohol, n-propanol, ethanol, methanol, NMP, NEP, DMF, or DMAc, and any combination thereof, and is more preferably a mixture of water, isopropyl alcohol and DMAc.

According to one particularly preferred embodiment of the preparation of a compound of formula (VI) or a salt thereof, preferably its monosodium salt (VII),

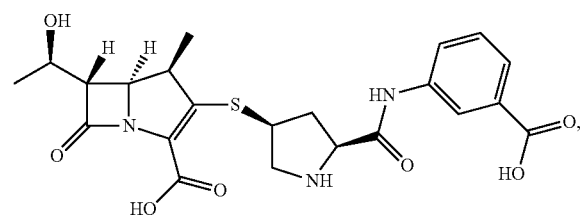

(VI)

step d) comprises converting a compound of formula

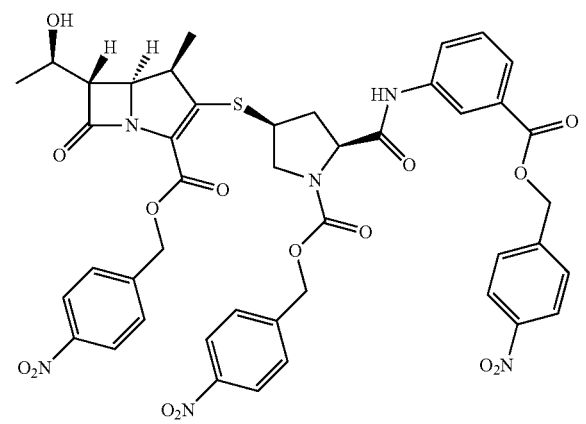

(Ia)

in crystalline form, to the compound of formula (VI) or a salt thereof, preferably its monosodium salt (VII), wherein in step d) hydrogen is added and wherein step d) is carried out in the presence of palladium-on-carbon and sodium hydrogen carbonate present in an amount of 5.5 equivalents with respect to the compound of formula (Ia), in a mixture of water, isopropyl alcohol and DMAc, at room temperature.

According to a further embodiment of step d), the used compound of formula (I) is in amorphous form. Step d) is then either carried out as described for the crystalline material or as follows: step d) is then typically carried out in the presence of a base and the base is present in an amount of 3.5 to 4.5 equivalents, particularly 3.7 to 4.2 equivalents, and more particularly 4.0 equivalents, with respect to the compound of formula (I) or a solvate thereof. Particularly, step d) is then carried out at a temperature of 0° C. to 20° C., particularly from 5° C. to 15° C., and more particularly 10° C. When step d) is carried out in a solvent, it is preferably selected from water, tetrahydrofuran, isopropyl alcohol, or DMAc, and any combination thereof, and is more preferably a mixture of water and isopropyl alcohol.

According to one particularly preferred embodiment of the preparation of a compound of formula (VI) or a salt thereof, preferably its monosodium salt (VII),

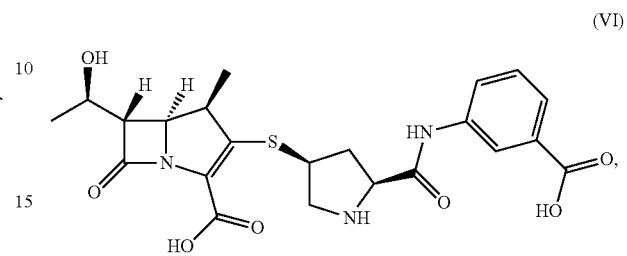

(VI)

step d) comprises converting a compound of formula

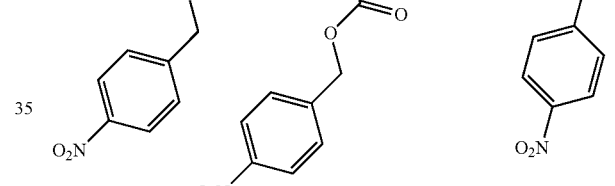

(Ia)

to the compound of formula (VI) or a salt thereof, preferably its monosodium salt (VII), wherein in step d) hydrogen is added and wherein step d) is carried out in the presence of palladium-on-carbon and sodium hydrogen carbonate present in an amount of 4.0 equivalents with respect to the compound of formula (Ia), in a mixture of water and isopropyl alcohol at 10° C.

The invention will be more fully understood by references to the following examples. They should not, however, be construed as limiting the scope of the invention. The disclosure of all literature and patent citations mentioned herein are expressly incorporated by reference.

EXAMPLES 1. (Ia) from (IVa)

A solution of (IVa) (1 g, 1.27 mmol) in DMF (5 mL) was cooled to 0° C. and p-nitrobenzylbromide (0.41 g, 1.90 mmol) was added, followed by triethylamine (0.263 mL) and the mixture was stirred at 0° C. for 5 h. The reaction was warmed to room temperature and p-nitrobenzylbromide (0.14 g, 0.64 mmol) was added. After 20.5 h at room temperature an additional amount of triethylamine (0.10 mL, 0.72 mmol) was added and stirring continued for 7 h. The mixture was diluted with ethylacetate and water and layers were separated, the aqueous layer was extracted with ethyl acetate. The combined organic layers were washed with water and concentrated to give 1 g residue.

2. Hydrogenation of (Ia)

To Pd/C (1.1 g, 10% Pd, 50% wet) in water (3 mL) and isopropyl alcohol (1 mL) in a hydrogenation vessel was added NaHCO$_3$ (370 mg, 4.4 mmol) and cooled to 10° C. To a solution of (Ia) (1 g, 1.1 mmol) in ethyl acetate (15 mL) was added isopropyl alcohol (2.5 mL) and an aqueous 5% NaHCO$_3$ solution (1.25 mL). The substrate solution was added to the catalyst solution in the autoclave and H$_2$ pressure (4 bar) was applied for 3 h under heavy stirring. The catalyst was filtered of and washed with isopropyl alcohol and water. The aqueous layer was washed with ethyl acetate and concentrated to 12 mL. Methanol and n-propanol was added and pH adjusted to 6.5 with acetic acid to give (VII).

3. Crystallization of Compound (Ia)

(Ia) (15.8 g, 17 mmol) was dissolved in ethyl acetate (150 mL) at room temperature and seeding crystals were added. After 17 h a thick suspension was formed and heptane (50 mL) was added. The mixture was cooled to 0° C. for 2 h and the crystals were filtered off, washed with heptane and dried under vacuo to give 13.42 g of crystalline material.

4. Hydrogenation of Crystalline (Ia)

NaHCO$_3$ (5.5 eq) was dissolved in water (170 g) and Pd/C (15 g; 10% Pd) and isopropyl alcohol (100 g) are added followed by a solution of 15 g (Ia) in DMAc (73 g). H$_2$ pressure (4 bar) was applied at 25° C. for 3 h under heavy stirring. The catalyst was filtered off and washed with isopropyl alcohol and water. The aqueous layer was extracted with ethyl acetate and the pH was adjusted to pH=5.5 with glacial acetic acid to give (VII). (VII) is then crystallized by addition of MeOH and isopropyl alcohol followed by seed crystals and cooling of the suspension to −20° C.

5. Crystalline (Ia) In Situ from (IIa) and (IIIa) and p-Nitrobenzylbromide

A solution of (IIIa) (1.09 eq) and (IIa) (1 eq) in DMAc (0.4M) was cooled to −20° C. and DIPEA (4.4 eq) is added. After 2 h a solution of p-nitrobenzylbromide (1.3 eq) in DMAc (2M) was added. The reaction was warmed to 35° C. and stirred for 3 h. DMAc was added to reach 0.16M. Excess base was quenched by the addition of AcOH (2.5 eq). Isopropyl alcohol and water were added, followed by seeding crystals. The mixture was stirred for another 20 h at 35° C. The suspension was cooled to room temperature, filtered and washed with isopropyl alcohol. The crystalline product was dried in vacuo.

$^1$H-NMR (500 MHz, d$^6$-DMSO): δ=10.32 (s, 1H), 8.30 (bs, 0.4H), 8.24 (d, J=8.51 Hz, 2H), 8.26 (bs, 0.6H), 8.19 (bd, J=8.51 Hz, 3H), 7.91 (bt, J=6.94 Hz, 1H), 7.87 (d, J=8.51 Hz, 1H), 7.72 (bd, J=8.51 Hz, 3H), 7.69 (d, J=8.51 Hz, 2H), 7.66 (d, J=8.51 Hz, 1H), 7.47 (d, J=7.88 Hz, 1H), 7.46 (d, J=8.51 Hz, 1H), 5.50 (s, 2H), 5.41 (d, J=14.19 Hz, 1H), 5.30 (d, J=13.87 Hz, 0.6H), 5.29 (d, J=14.02 Hz, 1H), 5.24 (s, 0.8H), 5.08 (d, J=5.04 Hz, 1H), 5.04 (d, J=13.87 Hz, 0.6H), 4.50 (t, J=7.72 Hz, 0.6H), 4.43 (t, J=7.72 Hz, 0.4H), 4.27 (dt, J=9.65, 0.70 Hz, 1H), 4.22 (dd, J=9.95, 7.39 Hz, 0.4H), 4.15 (dd, J=10.40, 7.25 Hz, 0.6H), 3.99 (m, 2H), 3.61 (m, 1H), 3.39 (t, J=9.30 HZ, 0.4H), 3.34 (t, J=9.30 Hz, 0.6H), 3.30 (dd, J=6.30, 2.52 Hz, 1H), 2.81 (m, 1H), 1.93 (m, 1H), 1.19 (d, J=7.25 Hz, 3H), 1.16 (d, J=6.30 Hz, 3H)

The X-ray powder diffractogram was obtained with a PANalytical X'Pert PRO diffractometer equipped with a theta/theta coupled goniometer in transmission geometry, Cu—Kα1,2 radiation (wavelength 0.15419 nm) with a focusing mirror and a solid state PIXcel detector. The diffractogram was recorded at a tube voltage of 45 kV and a tube current of 40 mA, applying a stepsize of 0.013° 2-Theta with 40 s per step (255 channels) in the angular range of 2° to 40° 2-Theta at ambient conditions (see FIG. 1 and table 1).

TABLE 1

| Pos. [°2Th.] | Rel. Int. [%] |
| --- | --- |
| 3.4 | 41 |
| 6.5 | 100 |
| 14.4 | 56 |
| 17.7 | 99 |
| 21.1 | 52 |
| 22.1 | 69 |

LIST OF REFERENCES

WO 9857973 A1
WO 9802439 A1
WO 2008062279 A2
WO 03026572 A2
IN 01890CH2007

The following pages of the description refer to the embodiments of the invention listed as separate items:

1. A compound of formula (I) or a solvate thereof

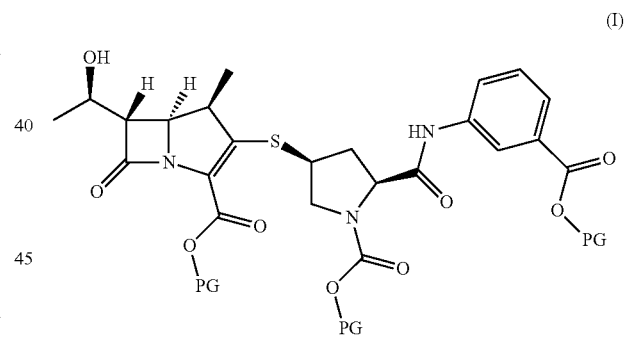

wherein the PG residues are each and independently a protective group, which is capable of protecting a carboxylic acid function.
2. The compound of item 1, wherein all PG residues are identical or wherein at least two of the PG residues are identical.
3. The compound of item 1, wherein the three PG residues are different.
4. The compound of any of items 1 to 3, wherein each PG residue is selected from benzyl, methylene substituted benzyl, p-substituted benzyl, o-substituted benzyl, or m-substituted benzyl groups, wherein the substituent is preferably selected from nitro, methoxy residues or halides; wherein the PG residue is more preferably selected from p-nitrobenzyl, o-nitrobenzyl, m-nitrobenzyl, p-methoxybenzyl, o-methoxybenzyl, or m-methoxybenzyl; p-chlorobenzyl, o-chlorobenzyl and is most preferably p-nitrobenzyl.

5. The compound of any of items 1 to 4, wherein the compound of formula (I) is in crystalline or in amorphous form.

6. The compound of item 1, wherein the compound of formula (I) is the compound of formula (Ia)

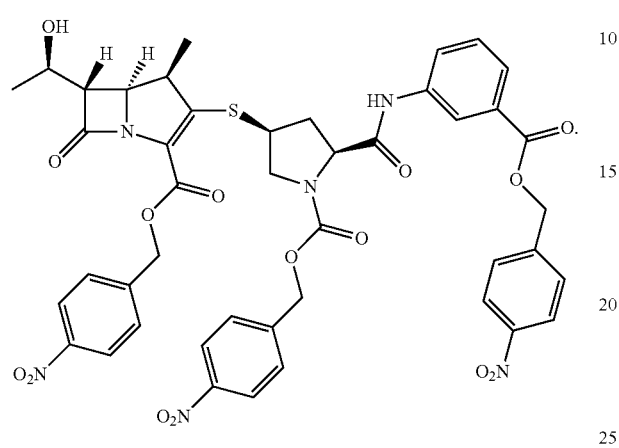

(Ia)

7. A crystalline compound of formula (Ia)

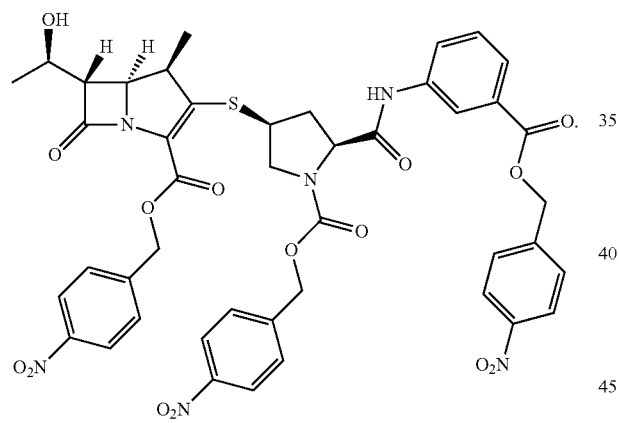

(Ia)

8. A crystalline compound of formula (Ia) obtained or obtainable by a process as defined herein.

9. The compound of items 7 or 8, wherein the compound of formula (Ia) is in crystalline form and is characterized by an X-ray powder diffraction pattern with peaks at 2-theta angels of about 3.4°, 6.5°, 14.4°, 17.7°, 21.1°, 22.1° when using Cu—Kα radiation.

10. Use of a compound of any of the preceding items in a process for the preparation of (4R,5S,6S)-3-[(3S,5S)-5-[(3-carboxyphenyl)carbamoyl]-pyrrolidin-3-yl]sulfanyl-6-(1-hydroxyethyl)-4-methyl-7-oxo-1-azabicyclo[3.2.0]hept-2-ene-2-carboxylic acid or a salt thereof.

11. Use of a compound of any of items 1 to 9 in a process for the preparation of (4R,5S,6S)-3-[(3S,5S)-5-[(3-carboxyphenyl)carbamoyl]-pyrrolidin-3-yl]sulfanyl-6-(1-hydroxyethyl)-4-methyl-7-oxo-1-azabicyclo[3.2.0]hept-2-ene-2-carboxylic acid or a salt thereof starting from the following compounds of formula (II) and (III) or a salt thereof

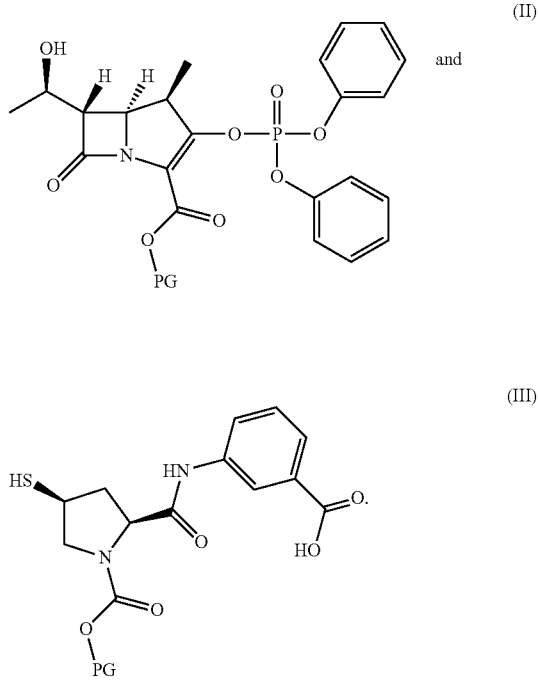

(II)

and

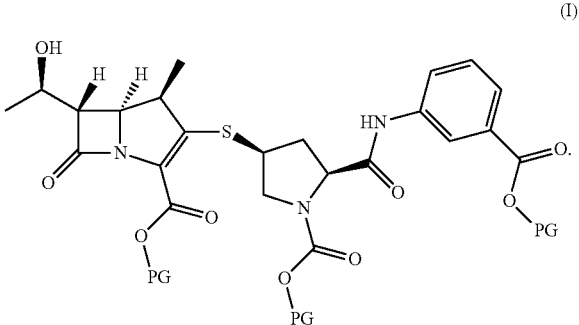

(III)

12. The process for the preparation of a compound of formula (I) or a solvate thereof

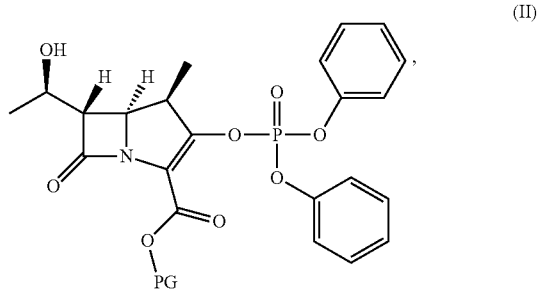

(I)

wherein the PG residues are as defined in any of items 1 to 4;

comprising a step a) of reacting a compound of formula (II), (II)

with a compound of formula (III) or a salt thereof,

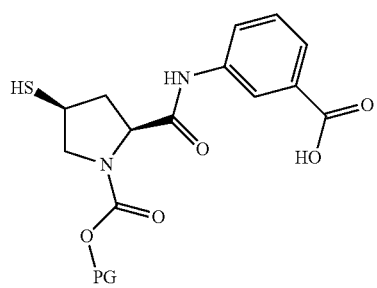
(III)

to obtain a compound of formula (IV) or a salt thereof

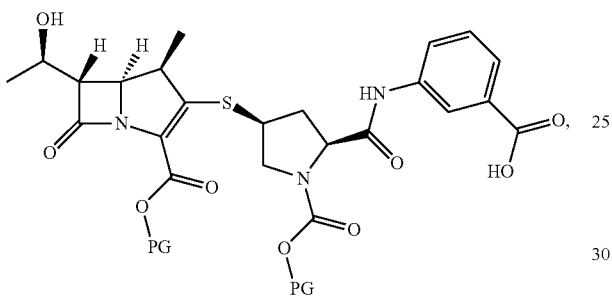
(IV)

and a step b) of converting the compound of formula (IV) or a salt thereof to the compound of formula (I) or a solvate thereof, and optionally a step c) of crystallizing the compound of formula (I) or a solvate thereof from a solution of the compound of formula (I).

13. A process for the preparation of a compound of formula (VI) or a salt thereof, preferably its monosodium salt of formula (VII),

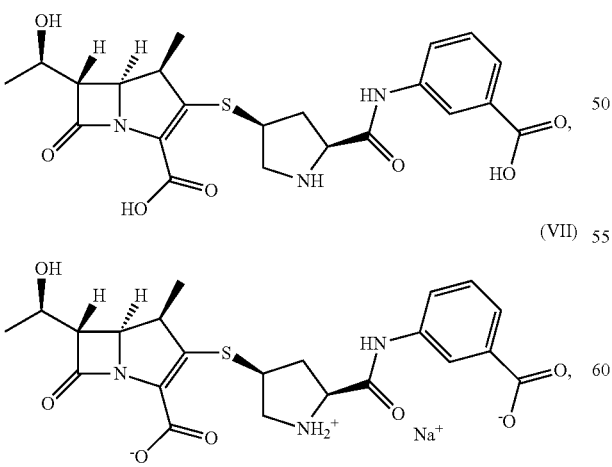
(VI)

(VII)

comprising a step a) of reacting a compound of formula (II),

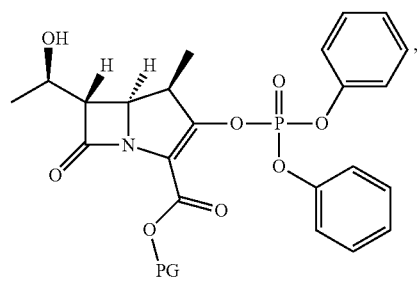
(II)

with a compound of formula (III) or a salt thereof, (III)

to obtain a compound of formula (IV) or a salt thereof

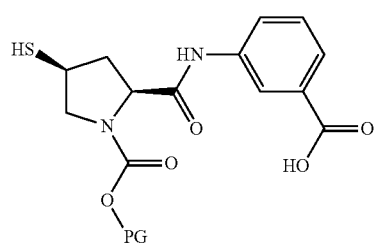
(IV)

and a step b) of converting the compound of formula (IV) or a salt thereof to a compound of formula (I) or a solvate thereof

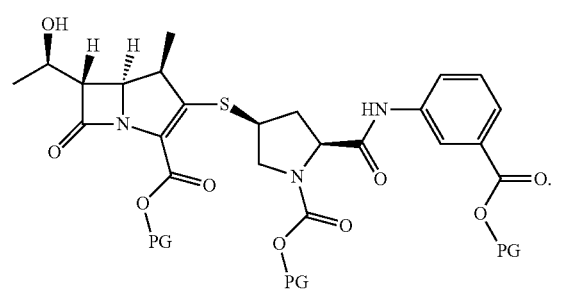
(I)

wherein the PG residues are defined in any of items 1 to 4;

and a step d) of converting the compound of formula (I) or a solvate thereof to the compound of formula (VI), optionally after a step c) of crystallizing the compound of formula (I) or a solvate thereof from a solution of the compound of formula (I).

14. The process for the preparation of a compound of formula (I) or a solvate thereof

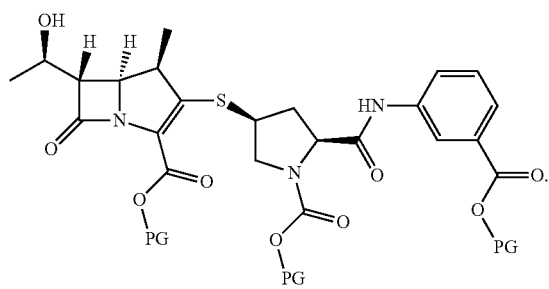

(I)

wherein the PG residues are defined in any of items 1 to 4;

comprising a step b) of converting a compound of formula (IV) or a salt thereof

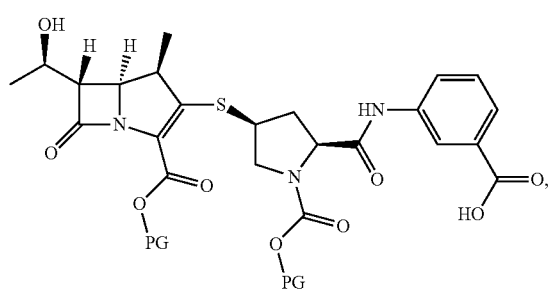

(IV)

to the compound of formula (I) or a solvate thereof, and optionally a step c) of crystallizing the compound of formula (I) or a solvate thereof from a solution of the compound of formula (I).

15. A process for the preparation of a compound of formula (VI) or a salt thereof, preferably its monosodium salt of formula (VII),

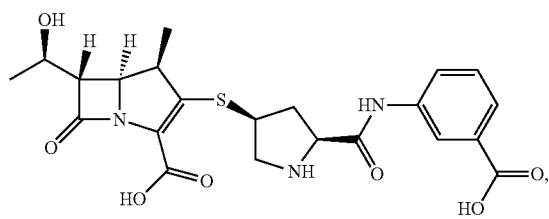

(VI)

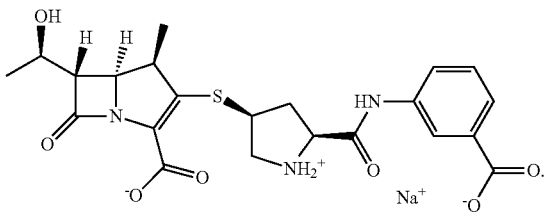

(VII)

comprising a step b) of converting a compound of formula (IV) or a salt thereof

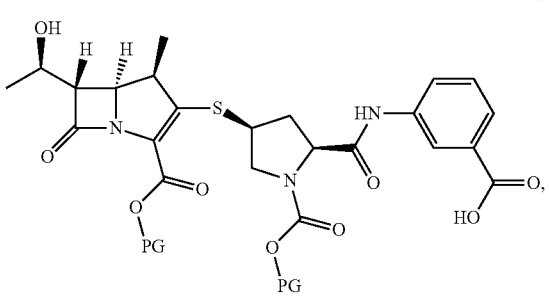

(IV)

to a compound of formula (I) or a solvate thereof

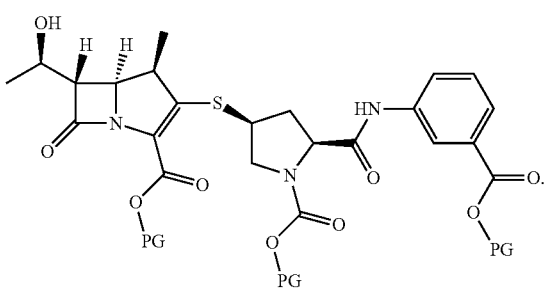

(I)

wherein the PG residues are as defined in any of items 1 to 4;

and a step d) of converting the compound of formula (I) or a solvate thereof to the compound of formula (VI), optionally after a step c) of crystallizing the compound of formula (I) or a solvate thereof from a solution of the compound of formula (I).

16. A process for the preparation of a compound of formula (VI) or a salt thereof, preferably its monosodium salt of formula (VII),

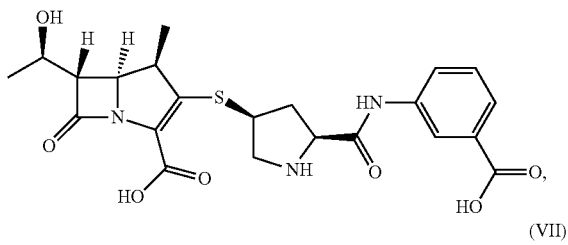

comprising a step d) of converting a compound of formula (I) or a solvate thereof

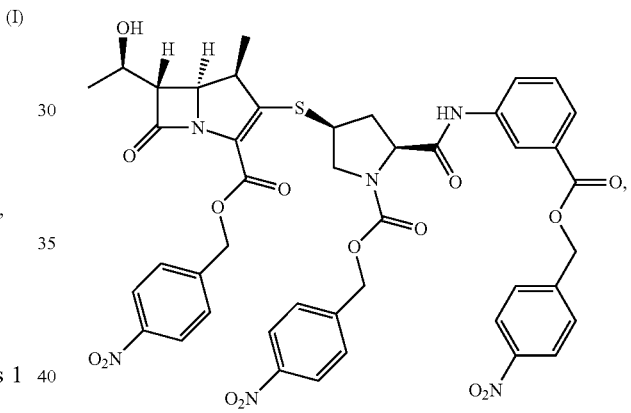

wherein the PG residues are as defined in any of items 1 to 4;
to the compound of formula (VI);
optionally after a step c) of crystallizing the compound of formula (I) or a solvate thereof from a solution of the compound of formula (I).

17. The process of items 12 or 13, wherein the compound of formula (IV) is used after step a) without purification and/or isolation of the compound of formula (IV) after step a).

18. The process of any of items 12 to 17, wherein the compound of formula (I) is the compound of formula (Ia) as defined in any of items 6 to 9.

19. The process of items any of items 12, 13, 17 and 18, wherein step a) is carried out at a temperature of −40° C. to 0° C., particularly from −30° C. to −10° C., and more particularly −20° C. to −15° C.

20. The process any of items 12, 13, and 17 to 19, wherein step a) is carried out in a solvent, particularly an aprotic solvent.

21. The process of any of items 12, 13, and 17 to 20, wherein step a) is carried out in a solvent selected from dimethylacetamide (DMAc), tetrahydrofuran (THF), dimethylformamide (DMF), 2-methyltetrahydrofuran, N-methyl-2-pyrrolidone (NMP), and any combination thereof, and is particularly DMAc.

22. The process of any of items 12, 13, and 17 to 21, wherein in step a) the compound of formula (III) or a salt thereof is present in an amount of 1.0 to 1.2 equivalents, particularly of 1.08 to 1.1 equivalents, and more particularly 1.09 equivalents, with respect to the compound of formula (II).

23. The process of any of items 12, 13, and 17 to 22, wherein step a) is carried out in the presence of a base.

24. The process of any of items 12, 13, and 17 to 23, wherein the base is present in an amount of 3.5 to 5.5 equivalents, particularly of 4.3 to 4.5 equivalents, and more particularly 4.4 equivalents, with respect to the compound of formula (II).

25. The process of items 23 or 24, wherein the base is selected from secondary and tertiary amines, particularly isopropylmethylamine, butylmethylamine, diisopropylethylamine and triethylamine; cyclic tertiary amines, particularly cis-2,6-dimethylpiperidine, 1,4-diazabicyclo[2.2.2]octane, N-methylpiperidine and N-methylmorpholine; and any combination thereof, and is preferably diisopropylethylamine.

26. The process of items 12 or 13, wherein the compound of formula (I) is the compound of formula (Ia)

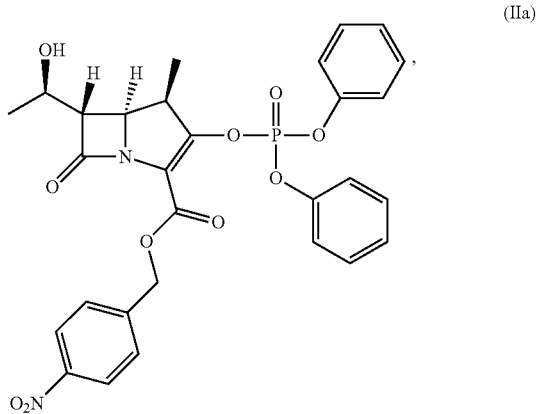 [SMILES: C[C@@H](O)[C@H]1C(=O)N2C(C(=O)OCc3ccc([N+](=O)[O-])cc3)=C(OP(=O)(Oc3ccccc3)Oc3ccccc3)[C@H](C)[C@H]12]

wherein the step a) comprises reacting a compound of formula (IIa), with a compound of formula (IIIa),

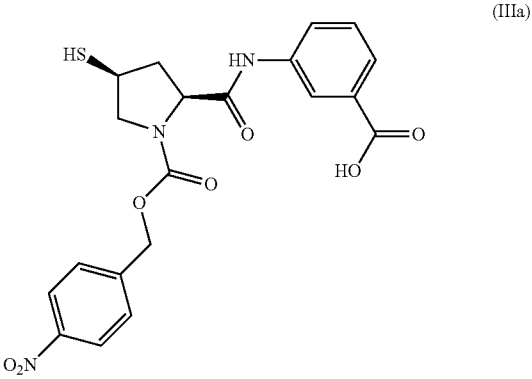 [SMILES: O=C(O)c1cccc(NC(=O)[C@@H]2C[C@H](S)CN2C(=O)OCc2ccc([N+](=O)[O-])cc2)c1]

to obtain a compound of formula (IVa)

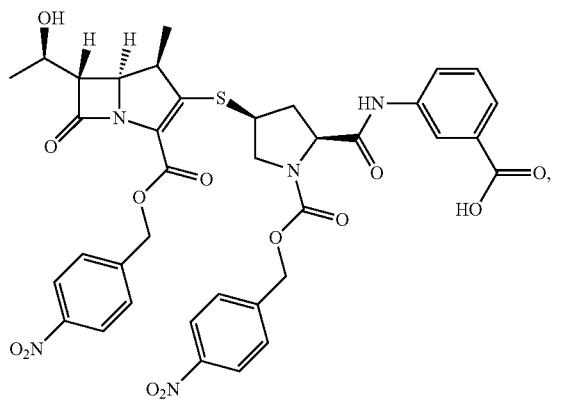

wherein step a) is carried out with 1.09 equivalents of the compound of formula (IIIa) in the presence 4.4 equivalents of diisopropylethylamine, each with respect to the compound of formula (IIa); at a temperature of −20° C. in DMAc.

27. The process of any of items 12, 13, and 17 to 26, wherein the compound of formula (IV) or a salt thereof is converted in step b) to the compound of formula (I) without purification and/or isolation of the compound of formula (IV) or a salt thereof after step a).

28. The process item 27, wherein step b) is carried out at a temperature of 25° C. to 45° C., particularly from 30° C. to 40° C., and more particularly at 35° C.

29. The process of item 27 or 28, wherein converting the compound of formula (IV) or a salt thereof to the compound of formula (I) or a solvate thereof is carried out by adding an agent suitable for introducing a protective group.

30. The process of any of items 27 to 29, wherein converting the compound of formula (IV) or a salt thereof to the compound of formula (I) or a solvate thereof is carried by adding a compound of formula (V)

PG-L   (V)

wherein the PG residues are as defined in any of items 1 to 4 and wherein L is a leaving group, wherein the compound is preferably added in the same solvent as used for step a).

31. The process of item 30, wherein L is selected from halides, particularly bromide and alkyl sulfonates and aryl sulfonates, and is preferably bromide.

32. The process of item 30 or 31, wherein PG residue is p-nitrobenzyl and the compound of formula (V) is selected from p-nitrobenzylbromide and p-nitrobenzylchloride, and is preferably p-nitrobenzylbromide.

33. The process of any of items 30 to 32, wherein the compound of formula (V) is present in an amount of 1 to 3 equivalents, particularly of 1.2 to 1.4 equivalents, and more particularly 1.3 equivalents, with respect to the compound of formula (II).

34. The process of any of items 12 to 15, and 17 to 26, wherein the compound of formula (I) is the compound of formula (Ia)

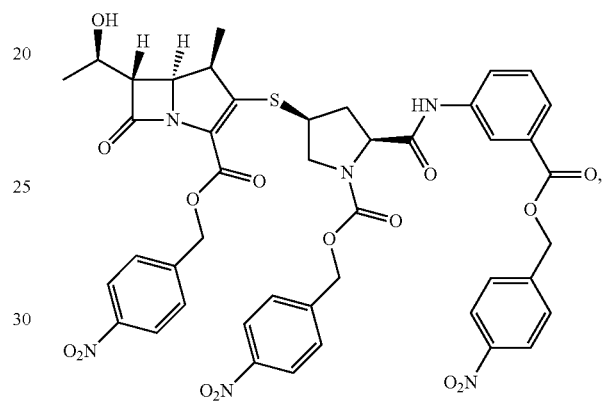

wherein step b) comprises converting a compound of formula (IVa)

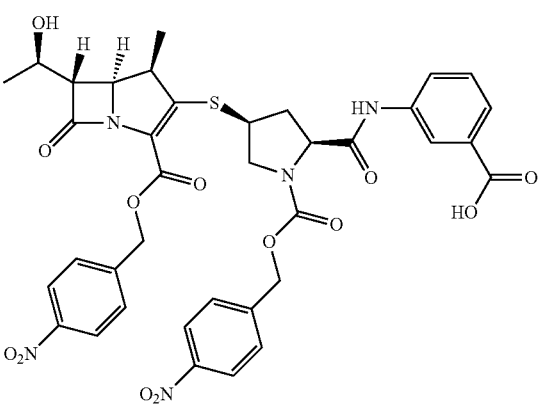

to the compound of formula (Ia), wherein step b) is carried out with 1.3 equivalents of p-nitrobenzylbromide with respect to the compound of formula (II); at a temperature of 35° C.

35. The process of any of items 12 to 15, and 18 to 26, wherein in step b) the compound of formula (IV) or a salt thereof is present in an amount of 1 equivalent.

36. The process of any of items 12 to 15, 18 to 26 and 35, wherein step b) is carried out at a temperature of 15° C. to 40° C., particularly from 20° C. to 30° C., and more particularly room temperature.

37. The process of any of items 12 to 15, 18 to 26, 35 and 36, wherein converting the compound of formula (IV) or a salt thereof to the compound of formula (I) is carried by adding an agent suitable for introducing a protective group.
38. The process of any of items 12 to 15, 18 to 26, and 35 to 37, wherein converting the compound of formula (IV) or a salt thereof to the compound of formula (I) or a solvate thereof is carried by adding a compound of formula (V)

PG-L   (V)

wherein the PG residues are as defined in any of items 1 to 4 and wherein L is a leaving group as defined in item 31.
39. The process of item 38, wherein the compound of formula (V) is present in an amount of 1.0 to 2.0 equivalents, particularly of 1.2 to 1.4 equivalents, and more particularly 1.3 equivalents, with respect to the compound of formula (IV) or a salt thereof.
40. The process of any of items 12 to 15, 18 to 26, and 35 to 39, wherein step b) is carried out in the presence of a base.
41. The process of item 40, wherein the base is present in an amount of 1.0 to 4.0 equivalents, particularly of 1.5 to 3 equivalents, and more particularly 2 equivalents, with respect to the compound of formula (I) or a solvate thereof.
42. The process of item 40 or 41, wherein the base is selected from secondary and tertiary amines, particularly isopropylmethylamine, butylmethylamine, diisopropylethylamine and triethylamine; cyclic tertiary amines, particularly cis-2,6-dimethylpiperidine, 1,4-diazabicyclo[2.2.2]octane, N-methylpiperidine and N-methylmorpholine; and any combination thereof, and is preferably triethylamine and diisopropylamine.
43. The process of any of items 12 to 15, 18 to 26, and 35 to 42, wherein step b) is carried out in a solvent, particularly an aprotic solvent.
44. The process of any of items 12 to 15, 18 to 26, and 38 to 46, wherein step b) is carried out in a solvent selected from dimethylformamide (DMF), dimethylacetamide (DMAc), tetrahydrofuran (THF), 2-methyltetrahydrofuran, N-Methyl-2-pyrrolidone (NMP), and any combination thereof, and is particularly DMAc.
45. The process of any of items 12 to 15 and 18 to 26, wherein the compound of formula (I) is the compound of formula (Ia)

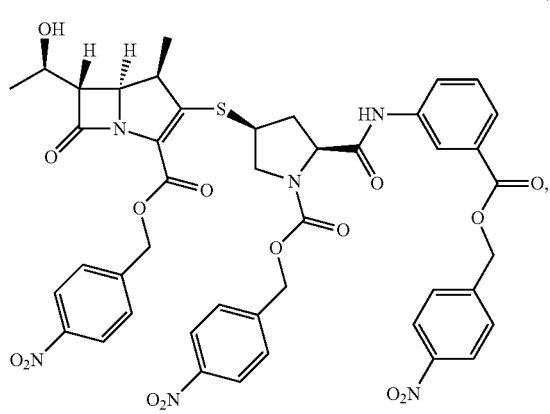

(Ia)

wherein step b) comprises converting a compound of formula (IVa)

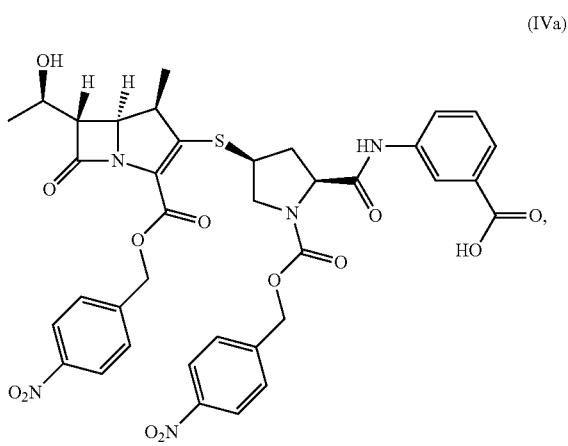 [SMILES: C[C@@H](O)[C@H]1C(=O)N2C(C(=O)OCc3ccc([N+](=O)[O-])cc3)=C(S[C@H]3C[C@@H](C(=O)Nc4cccc(C(=O)O)c4)N(C(=O)OCc4ccc([N+](=O)[O-])cc4)C3)[C@H](C)[C@H]12]

(IVa)

to the compound of formula (Ia), wherein step b) is carried is out with 1.3 equivalents p-nitrobenzylbromide and 1.0 equivalent of a compound of formula (IVa) in the presence of 2 equivalents of triethylamine or diisopropylethylamine, each with respect to the compound of formula (IVa); at room temperature in DMAc.
46. A process for the preparation of a compound of formula (I) or a solvate thereof as defined in any of items 1 to 9, particularly a compound of formula (Ia) or a solvate thereof, in crystalline form, preferably as defined in any of items 6 to 9, comprising a step c) of crystallizing the compound of formula (I) from a solution of the compound of formula (I).
47. The process of any of items 12 to 46, wherein step c) comprises a step h) of adding seeding crystals to a solution of a compound of formula (I) or a solvate thereof.
48. The process of item 47, wherein the solution comprises the compound of formula (I) in a concentration of 0.05 to 0.20 mol/L, particularly of 0.10 to 0.14 mol/L, and more particularly 0.11 mol/L.
49. The process of item 47 or 48, wherein the solvent used for the solution is an aprotic solvent.
50. The process of any of items 47 to 49, wherein the solvent used for the solution is selected from ethyl acetate and heptane, and any combination thereof, and is particularly ethyl acetate.
51. The process of any of items 47 to 50, wherein step c) is carried out at a temperature of −10° C. to 35° C., particularly from 10° C. to 25° C., and more particularly 25° C.

52. The process of item 46, wherein the compound of formula (I) is the compound of formula (Ia)

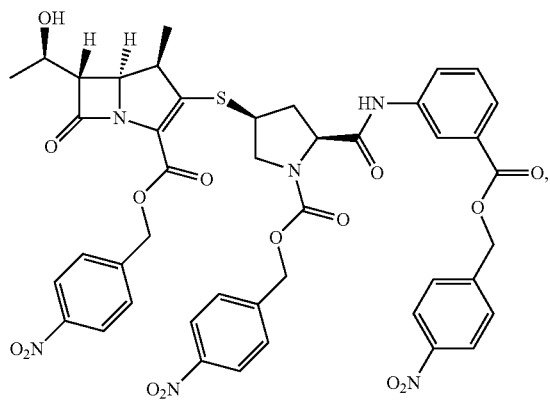

(Ia)

wherein the process comprises a step h) of adding seeding crystals to a solution of a compound of formula (Ia), wherein step c) is carried out at 25° C. in ethyl acetate comprising the compound of formula (Ia) in a concentration of 0.11 mol/L.

53. The process of any of items 12 to 34, 46 and 47 comprising a step c) of crystallizing the compound of formula (I) or a solvate thereof, wherein step c) is carried out without purification and/or isolation of the compound of formula (I) or a solvate thereof after a step b) has been carried out preferably as defined in any of items 27 to 34.

54. The process of any of items 12, 13, 17 to 34, 46 and 47 comprising a step c) of crystallizing the compound of formula (I) or a solvate thereof, wherein step c) is carried out without purification and/or isolation of the compound of formula (I) or a solvate thereof after step b) has been carried out preferably as defined in any of items 27 to 34 and wherein step b) is carried out without purification and/or isolation of after a step a) has been carried out preferably as defined in any of items 18 to 26.

55. The process of items 53 or 54, wherein the solvent used for the solution is the solvent as used in step b).

56. The process of any of items 53 to 55, wherein step c) comprises a step e), wherein in step e) the concentration of the compound of formula (I) or a solvate thereof in the solution is adjusted to be in the range of 0.14 to 0.18 M, particularly of 0.15 to 0.17 M, and more particularly 0.16 M, preferably by adding further solvent used for the solution, preferably DMAc.

57. The process of any of items 53 to 56, wherein step c) comprises a step f), preferably after a step e) as defined in item 56, wherein step f) acid is added to quench excess base, wherein the acid is preferably AcOH, HCl, and is more preferably AcOH.

58. The process of any of items 50 to 54, wherein step c) comprises a step g), preferably after a step f) as defined in item 57, wherein in step g) an anti-solvent is added wherein the anti-solvent is preferably selected from isopropyl alcohol, n-propanol, ethanol, methanol and water, and any combination thereof, and is preferably isopropyl alcohol and water.

59. The process of any of items 53 to 58, wherein step c) comprises a step h), preferably after a step g) as defined in item 58, of adding seeding crystals to a solution of a compound of formula (I) or a solvate thereof.

60. The process of any of items 53 to 59, wherein step c) is carried out at a temperature of 10° C. to 40° C., particularly from 32° C. to 38° C., and more particularly 35° C.

61. The process of item 46 wherein the compound of formula (I) is the compound of formula (Ia)

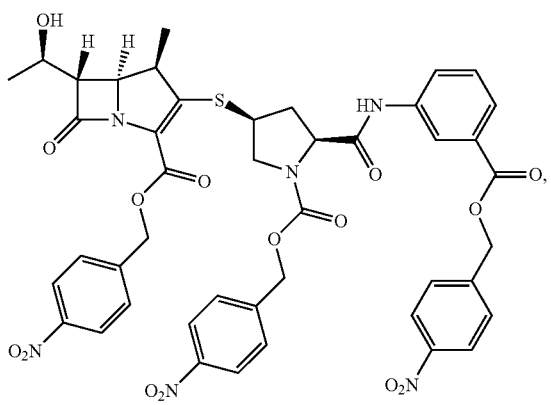

(Ia)

comprising step a) of reacting a compound of formula (IIa),

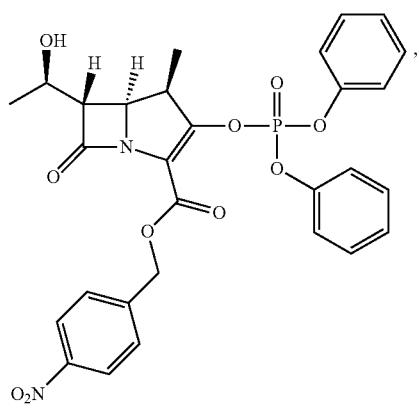

(IIa)

with a compound of formula (IIIa),

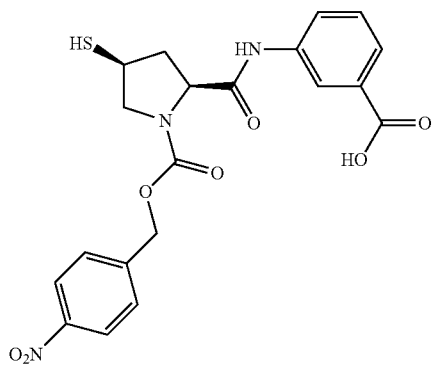

(IIIa)

to obtain a compound of formula (IVa)

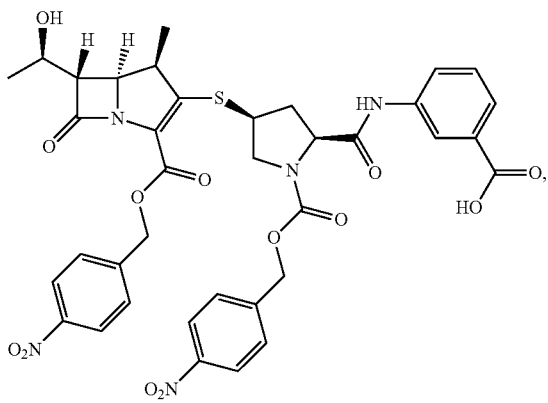

(IVa)

wherein step a) carried out with 1 equivalent of the compound of formula (IIa) and 1.09 equivalents of the compound of formula (IIIa) in the presence 4.4 equivalents of diisopropylethylamine, each with respect to the compound of formula (IIa), at a temperature of −20° C. in DMAc;

a step b) of converting the compound of formula (IVa) to the compound of formula (Ia), wherein step b) is carried out with 1.3 equivalents of p-nitrobenzylbromide with respect to the compound of formula (IIa); at 35° C., and wherein the compound of formula (IVa) has been obtained after the step a) and is used without purification and/or isolation of the compound of formula (IVa) after step a); and a step c) of crystallizing the compound of formula (Ia), wherein step c) comprises a step e), wherein in step e) the concentration of the compound of formula (Ia) in the solution is adjusted to be 0.16 M by adding further DMAc;

a step f), wherein in step f) AcOH is added;

a step g), wherein in step g) isopropyl alcohol and water are added; and a step h), wherein in step h) seeding crystals are added at a temperature of 35° C.

62. The process of item 13, 15 or 16, wherein the compound of formula (VI) is produced in form of a salt, preferably in form of its sodium, potassium, or lithium salt, more preferably in form of its monosodium salt (VII).

63. The process of item 13, 15, 16 or 62, wherein in step d) an agent suitable for removing the PG residues is added.

64. The process of item 13, 15, 16, 62 or 63, wherein step d) is carried out in the presence of a catalyst.

65. The process of any of items 13, 15, 16, and 62 to 64, wherein when the PG residues are as defined in any of items 1 to 4, the agent suitable for removing the PG residue is hydrogen.

66. The process of any of items 13, 15, 16, and 62 to 65, wherein when the PG residue is as defined in any of items 1 to 4, the catalyst is selected from the group consisting of solid-supported metal catalysts, preferably palladium-on-carbon, platinum-on-carbon, platinum-vanadium-on-carbon, and palladium hydroxid, and is more preferably palladium-on-carbon.

67. The process of any of items 13, 15, 16, and 62 to 66, wherein step d) is carried out in the presence of a base.

68. The process of item 67, wherein the base is selected from basic inorganic salts, particularly from sodium hydrogen carbonate, sodium carbonate, potassium carbonate, or calcium acetate, particularly sodium hydrogen carbonate and sodium carbonate; and any combination thereof, and is preferably sodium hydrogen carbonate.

68. The process of any of items 62 to 68, wherein the compound of formula (I) is in crystalline form as defined in items 7 to 9.

69. The process of items 68, wherein step d) is carried out in the presence of a base and the base is present in an amount of 3.5 to 7 equivalents, particularly 4.5 to 6.5 equivalents, and more particularly 5.5 equivalents, with respect to the compound of formula (I).

70. The process of items 68 or 69, wherein step d) is carried out at a temperature of 15° C. to 40° C., particularly from 20° C. to 30° C., and more particularly room temperature.

71. The process of any of items 68 to 70, wherein step d) is carried out in a solvent, preferably selected from water, tetrahydrofuran, isopropyl alcohol, n-propanol, ethanol, methanol, NMP, NEP, DMF, or DMAc, and any combination thereof, and is more preferably a mixture of water, isopropyl alcohol and DMAc.

72. The process of any of items 13, 15, 16 or 62, for the preparation of a compound of formula (VI)

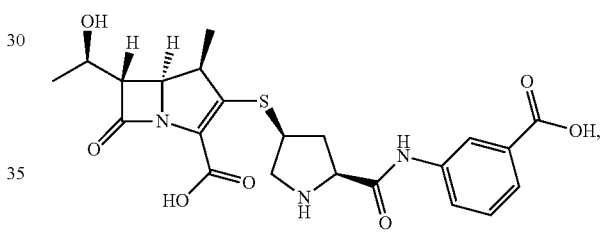

(VI)

wherein step d) comprise converting a compound of formula

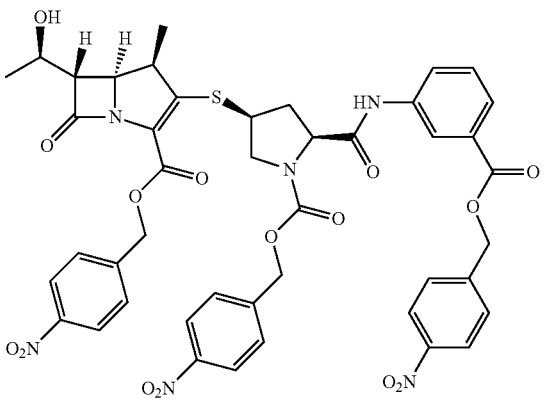

(Ia)

in crystalline form, to the compound of formula (VI), wherein in step d) hydrogen is added and wherein step d) is carried out in the presence of palladium-on-carbon and sodium hydrogen carbonate present in an amount of 5.5 equivalents with respect to the compound of formula (Ia), in a mixture of water, isopropyl alcohol and DMAc, at room temperature.

73. The process of any of items 13, 15, 16, and 62 to 68, wherein step d) is carried out in the presence of a base and the base is present in an amount of 3.5 to 4.5 equivalents, particularly 3.7 to 4.2 equivalents, and more particularly 4.0 equivalents, with respect to the compound of formula (I) or a solvate thereof.

74. The process of item 73, wherein step d) is carried out at a temperature of 0° C. to 20° C., particularly from 5° C. to 15° C., and more particularly 10° C.

75. The process of items 73 or 74, wherein step d) is carried out in a solvent, preferably selected from water, tetrahydrofuran, isopropyl alcohol, or DMAc, and any combination thereof, and is more preferably a mixture of water and isopropyl alcohol.

76. The process of any of items 13, 15, 16 or 62 for the preparation of a compound of formula (VI) or a salt thereof, preferably its monosodium salt (VII),

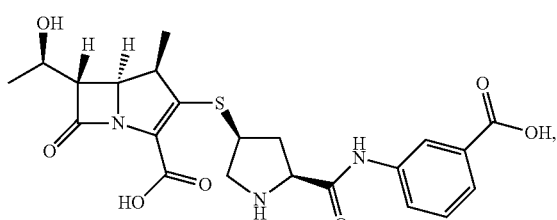
(VI)

comprising a step d) of converting a compound of formula

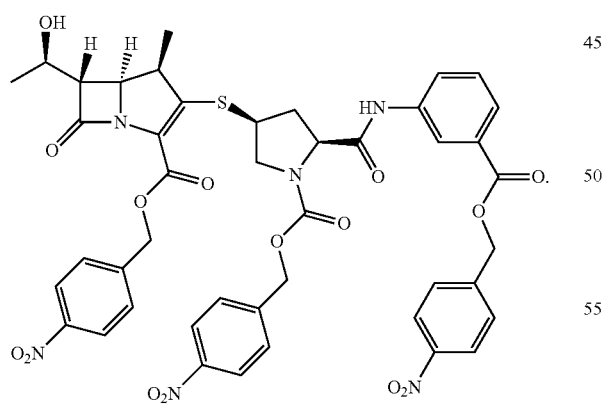
(Ia)

to the compound of formula (VI) or a salt thereof, preferably its monosodium salt (Vii), wherein in step d) hydrogen is added and wherein step d) is carried out in the presence of palladium-on-carbon and sodium hydrogen carbonate present in an amount of 4.0 equivalents with respect to the compound of formula (Ia), in a mixture of water and isopropyl alcohol at 10° C.

The invention claimed is:

1. A process for the preparation of a compound of formula (VI) or a salt thereof,

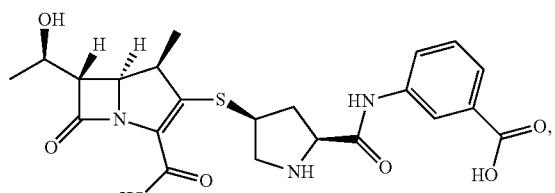
(IV)

comprising a step d) of converting a crystalline compound of formula (I) or a solvate thereof

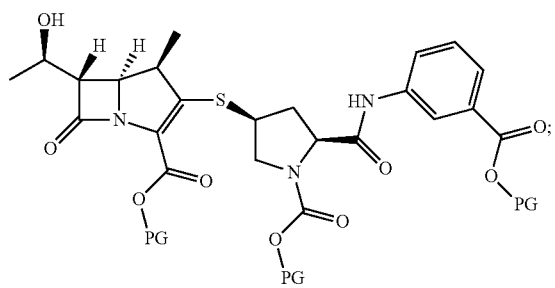
(I)

to the compound of formula (VI); wherein the PG residues are each and independently a protective group, which is capable of protecting a carboxylic acid function.

2. The process of claim 1, wherein the compound of formula (VI) is the monosodium salt of formula (VII),

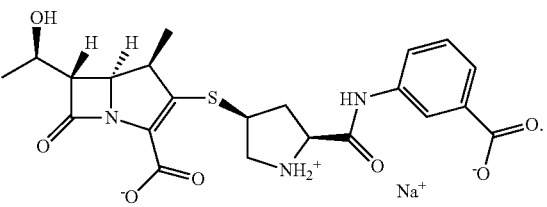
(VII)

3. The process of claim 1, wherein the compound of formula (I) is a compound of formula (Ia):

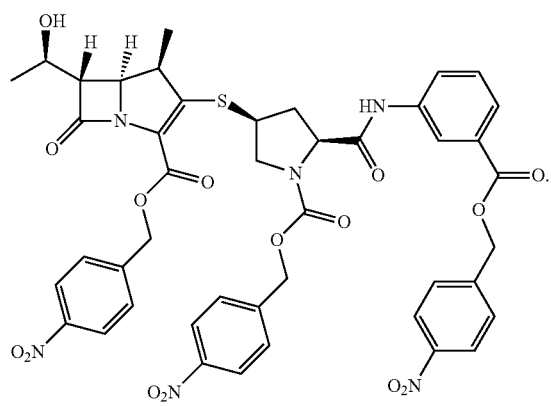

(Ia)

4. The process of claim 1, further comprising a step b) of converting a compound of formula (IV) or a salt thereof

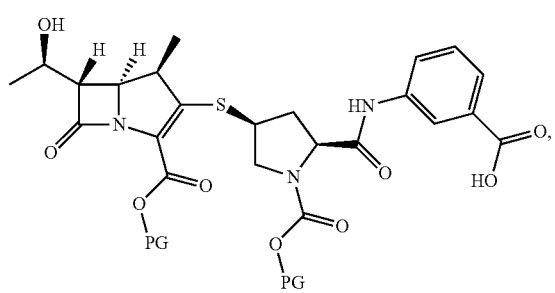

(IV)

to a compound of formula (I) or a solvate thereof

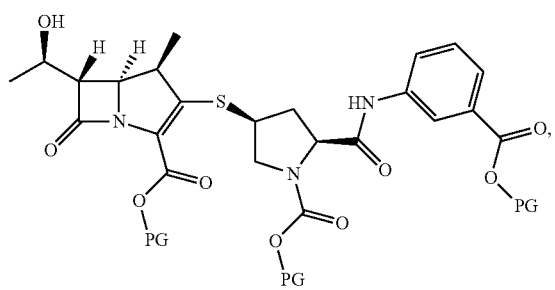

(I)

wherein the PG residues are each and independently a protective group, which is capable of protecting a carboxylic acid function;

and a step c) of crystallizing the compound of formula (I) or a solvate thereof from a solution of the compound of formula (I).

5. The process of claim 4, wherein the compound of formula (VI) is the monosodium salt of formula (VII),

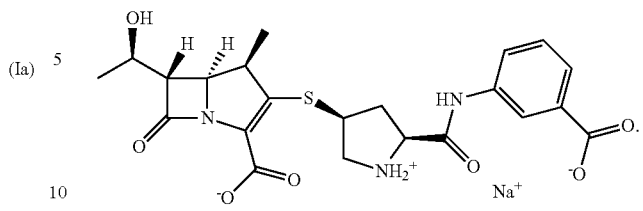

(VII)

6. The process of claim 4, wherein the compound of formula (I) is a compound of formula (Ia):

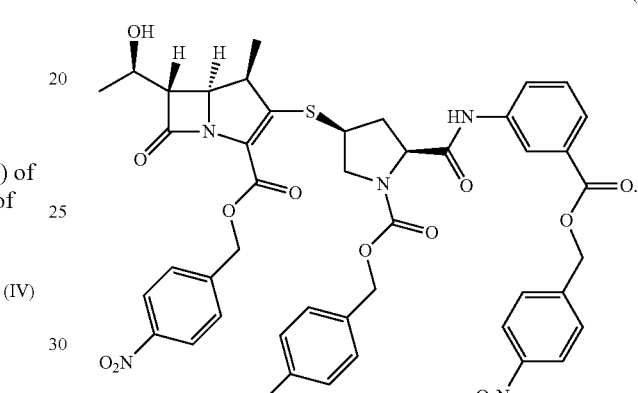

(Ia)

7. The process of claim 1, further comprising a step a) of reacting a compound of formula (II),

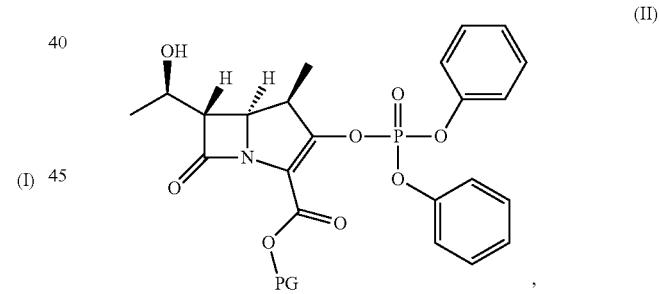

(II)

with a compound of formula (III) or a salt thereof,

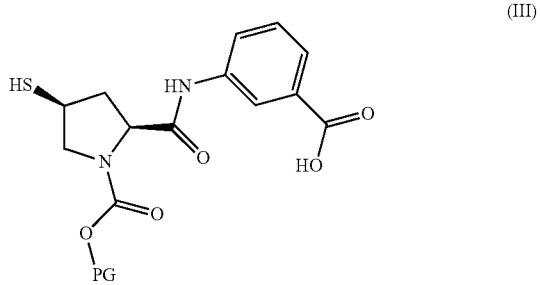

(III)

to obtain a compound of formula (IV) or a salt thereof

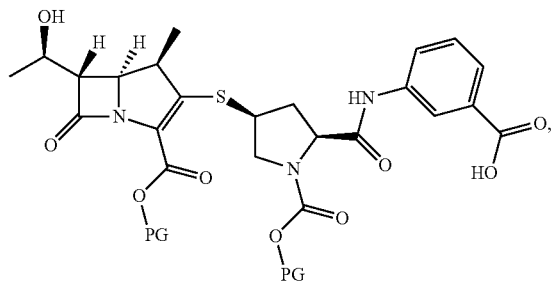

(IV)

and a step b) of converting the compound of formula (IV) or a salt thereof to a compound of formula (I) or a solvate thereof (I)

wherein the PG residues are each and independently a protective group, which is capable of protecting a carboxylic acid function;

and a step c) of crystallizing the compound of formula (I) or a solvate thereof from a solution of the compound of formula (I).

8. The process of claim 7, wherein the compound of formula (VI) is the monosodium salt of formula (VII), (VII)

* * * * *

UNITED STATES PATENT AND TRADEMARK OFFICE
CERTIFICATE OF CORRECTION

PATENT NO. : 9,546,171 B2  
APPLICATION NO. : 14/434550  
DATED : January 17, 2017  
INVENTOR(S) : Hannes Lengauer et al.

It is certified that error appears in the above-identified patent and that said Letters Patent is hereby corrected as shown below:

In the Claims

At Column 46, Claim 1, Line 6, replace "(IV)" with -- (VI) --

Signed and Sealed this  
Eighteenth Day of July, 2017

Joseph Matal  
*Performing the Functions and Duties of the*  
*Under Secretary of Commerce for Intellectual Property and*  
*Director of the United States Patent and Trademark Office*